United States Patent [19]

Jikihara et al.

[11] Patent Number: 4,960,897
[45] Date of Patent: Oct. 2, 1990

[54] HERBICIDE CONTAINING 1-(HALOGENOMETHYL)-VINYL PYRIDINES

[75] Inventors: Tetsuo Jikihara, Komae; Manabu Katsurada, Yokohama; Toyohiko Shike, Machida; Emiko Mikami; Osamu Ikeda, both of Machida, all of Japan

[73] Assignee: Mitsubishi Kasei Corporation, Tokyo, Japan

[21] Appl. No.: 163,086

[22] Filed: Mar. 2, 1988

[30] Foreign Application Priority Data

Mar. 4, 1987 [JP] Japan .................................. 62-49434
Mar. 10, 1987 [JP] Japan .................................. 62-54753

[51] Int. Cl.$^5$ ............................................ C07D 213/26
[52] U.S. Cl. .................................... 546/346; 546/345; 546/302; 546/290; 546/339; 546/270; 546/274; 546/268; 546/294; 546/295; 546/331; 71/94
[58] Field of Search ............... 546/345, 346, 302, 290, 546/339

[56] References Cited

U.S. PATENT DOCUMENTS 4,468,245  8/1984  Takematsu et al. ...................... 71/88
4,474,602  10/1984  Markley et al. ......................... 71/94

FOREIGN PATENT DOCUMENTS 46743 of 1979 Japan .
55-364 of 1981 Japan .
32267 of 1982 Japan .
286366 of 1986 Japan .

OTHER PUBLICATIONS

CA 109: 109196 h, Katritzky et al.

Primary Examiner—Jane T. Fan
Attorney, Agent, or Firm—Oblon, Spivak, McClelland, Maier & Neustadt

[57] ABSTRACT

Disclosed herein is an N-[2-(pyridyl)propyl]-N-substituted sulfonamide represented by the following general formula (I):

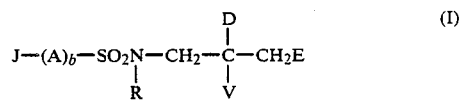

wherein J represents a phenyl group which may be substituted or benzo-condensed, A represents —$CH_2$—, —CH=CH—, —O— or —N(r)— (wherein r represents an alkyl group having 1 to 4 carbon atoms), b represents 0 or 1, R represents an alkyl group, alkenyl group, alkynyl group, alkoxy group, fluoroalkyl group or formyl group, D represents a hydroxyl group, E represents a halogen atom, an alkylsulfonyloxy group or a benzenesulfonyloxy group which may be substituted, or D and E represent —O— in combination, and V represents a pyridyl group which may be substituted, a herbicide containing said N-[2-(pyridyl)propyl]-N-substituted sulfonamide as an active ingredient and a 1-(halogenomethyl)vinylpyridine as an intermediate thereof.

5 Claims, No Drawings

HERBICIDE CONTAINING 1-(HALOGENOMETHYL)-VINYL PYRIDINES

BACKGROUND OF THE INVENTION

The present invention relates to a novel N-[2-(pyridyl)propyl]-N-substituted sulfonamide, a herbicide containing the same as an active ingredient and an intermediate thereof. More particularly, the present invention relates to an N-[2-(pyridyl)propyl]-N-substituted sulfonamide represented by the following general formula (I):

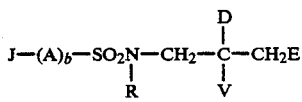

wherein J represents a phenyl group which may be substituted or benzo-condensed, A represents —$CH_2$—, —CH=CH—, —O— or —N(r)— (wherein r represents an alkyl group having 1 to 4 carbon atoms), b represents 0 or 1, R represents an alkyl group, an alkenyl group, an alkynyl group, an alkoxy group, a fluoroalkyl group or a formyl group, D represents a hydroxyl group, E represents a halogen atom, an alkylsulfonyloxy group or a benzenesulfonyloxy group which may be substituted or D and E represent —O— in combination, and V represents a pyridyl group which may be substituted, a herbicide containing said N-[2-(pyridyl)propyl]-N-substituted sulfonamide as an active ingredient and a 1-(halogenomethyl)vinylpyridine as an intermediate thereof.

Many sulfonamide compounds have conventionally been proposed as a herbicide. For example, Japanese Patent Publication No. 56-8027 (1981) discloses N-methyl-N-α,α-dimethylbenzylbenzenesulfonamide. The present inventors have proposed N-(2,3-epoxypropylene)-N-aralkylsulfonamides such as N-(2,3-epoxypropylene)-N-α-methylbenzylbenzene sulfonamide [Japanese Patent Application Laid-Open (KOKAI) No. 58-131977 (1983)] as a selective herbicide. Japanese Patent Application Laid-Open (KOKAI) Nos. 57-32267 (1982) and 61-286366 (1986) disclose sulfonamides having a pyridyl group as a compound having a herbicidal activity or a fungicidal activity.

On the other hand, 1-(halogenomethyl)vinylpyridines in the present invention are novel compounds which have not been reported in any publication. As the related arts to 1-(halogenomethyl)vinylpyridines of the present invention, for example, L. F. Hatch and T. L. Patton, J. Am. Chem. Soc., 76, 2705 (1954) disclose a method of preparing 3-chloro (or 3-bromo)-2-phenylpropene; M. G. Voronkov, et al, Zh. Org. Khim., 8(11) 2347(1972) disclose a method of producing 3-chloro-2-(4-methylphenyl)propene; U. K. Pandit and H. Bieraugel, Recl. Trav. Chim. Pays-Bas, 95(9) 223(1976) disclose 3-bromo-2-(3-methoxyphenyl)propene as an intermediate for the synthesis of 6-methyl-19-norsteroid; European Patent Application No. 94167A discloses 3-bromo-2-(4-chlorophenyl)propene as an intermediate for the production of an azole fungicide; and V. V. Dhekne et al, Indian J. Chem. Sect. B, 19B(3) 188(1980) describe a method of preparing 3-bromo-2-(2-methoxy-4-methylphenyl)propene.

As 1-(substituted methyl)vinylpyridines described in publications, 2-(1-hydroxy (or acetoxy) methylvinyl)-pyridine [Acta Chim. Scand. Ser. B, B29 (10) 985(1975) and Prom-st. Sint. Kauch, 1978 (8)2]; 4-(1-hydroxymethylvinyl)pyridine and 2-(1-hydroxymethylvinyl)-6-methylpyridine [Prom-st. Sint. Kauch 1978 (8)2]; 2-[1-(N,N-diethylaminomethyl)vinyl]-5-vinylpyridine [Khim. Geterotsikl. Soedin., 1968 (1) 128]; 4-(1-trimethylsilylmethylvinyl)pyridine [Bull. Chem. Soc. Jpn., 57(7), 1994 (1984)], etc. are known. All of these are, however, unsuitable as an intermediate for producing a sulfonamide having a herbicidal activity in accordance with the present invention in the respect of the reactivity.

Accordingly, it is desired to provide a herbicide which has a higher herbicidal activity than a conventional known sulfonamide compound and has a continuous herbicidal activity on weeds such as Echinochloa crus-galli in a long period from before the germination to an advanced stage of growing.

As a result of the studies undertaken by the present inventors, it has been found that N-[2-(pyridyl)propyl]-N-substituted sulfonamides represented by the following general formula (I):

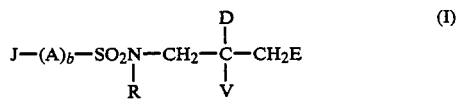

wherein J represents a phenyl group which may be substituted or benzo-condensed, A represents —$CH_2$—, —CH=CH—, —O— or —N(r)— (wherein r represents an alkyl group having 1 to 4 carbon atoms), b represents 0 or 1, R represents an alkyl group, an alkenyl group, an alkynyl group, an alkoxy group, a fluoroalkyl group or a formyl group, D represents a hydroxyl group, E represents a halogen atom, an alkylsulfonyloxy group or a benzenesulfonyloxy group which may be substituted, or D and E represent —O— in combination, and V represents a pyridyl group which may be substituted, have a very strong herbicidal effect on Echinochloa crus-galli from before the germination to an advanced stage of growing and cause little damage to paddy-rice plants. On the basis of this finding, the present invention has been achieved.

SUMMARY OF THE INVENTION

In a first aspect of the present invention, there is provided a N-[2-(pyridyl)propyl]-N-substituted sulfonamide represented by the following general formula (I):

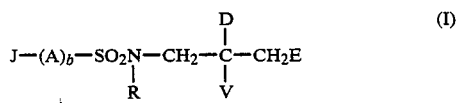

wherein J represents a phenyl group which may be substituted or benzo-condensed, A represents —$CH_2$—, —CH=CH—, —O— or —N(r)— (wherein r represents an alkyl group having 1 to 4 carbon atoms), b represents 0 or 1, R represents an alkyl group, an alkenyl group, an alkynyl group, an alkoxy group, a fluoroalkyl group or a formyl group, D represents a hydroxyl group, E represents a halogen atom, an alkylsulfonyloxy group or a benzenesulfonyloxy group which may be substituted, or D and E represent —O— in combination, and V represents a pyridyl group which may be substituted.

In a second aspect of the present invention, there is provided a herbicide containing as an active ingredient an N-[2-(pyridyl)propyl]-N-substituted sulfonamide represented by the following general formula (I):

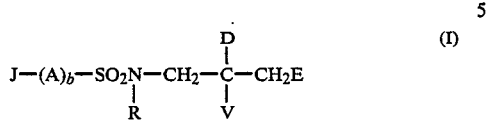

wherein J represents a phenyl group which may be substituted or benzo-condensed, A represents —CH$_2$—, —CH=CH—, —O— or —N(r)— (wherein r represents an alkyl group having 1 to 4 carbon atoms), b represents 0 or 1, R represents an alkyl group, an alkenyl group, an alkynyl group, an alkoxy group, a fluoroalkyl group or a formyl group, D represents a hydroxyl group, E represents a halogen atom, an alkylsulfonyloxy group or a benzenesulfonyloxy group which may be substituted, or D and E represent —O— in combination, and V represents a pyridyl group which may be substituted.

In a third aspect of the present invention, there is provided a 1-(halogenomethyl)vinylpyridine represented by the following general formula (V):

wherein u represents a halogen atom, and V represents a pyridyl group which may be substituted.

DETAILED DESCRIPTION OF THE INVENTION

A heart of the present invention lies in an N-[2-(pyridyl)propyl]-N-substituted sulfonamide represented by the following general formula (I):

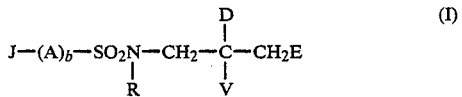

wherein J represents a phenyl group which may be substituted or benzo-condensed, A represents —CH$_2$—, —CH=CH—, —O— or —N(r)— (wherein r represents an alkyl group having 1 to 4 carbon atoms), b represents 0 or 1, R represents an alkyl group, an alkenyl group, an alkynyl group, an alkoxy group, a fluoroalkyl group or a formyl group, D represents a hydroxyl group, E represents a halogen atom, an alkylsulfonyloxy group or a benzenesulfonyloxy group which may be substituted, or D and E represent —O— in combination, and V represents a pyridyl group which may be substituted, a herbicide containing said N-[2-(pyridyl)propyl]-N-substituted sulfonamide as an active ingredient, and a 1-(halogenomethyl)vinylpyridine which is an intermediate of said N-[2-(pyridyl)propyl]-N-substituted sulfonamide and which is represented by the following general formula (V):

wherein u represents a halogen atom, and V a pyridyl group which may be substituted.

An N-[2-(pyridyl)propyl]-N-substituted sulfonamide used as a herbicide in the present invention is represented by the above-described general formula (I). In the general formula (I), J preferably represents a phenyl group represented by the formula:

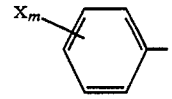

wherein X represents a halogen atom, preferably fluorine atom, chlorine atom, bromine atom; an alkyl group, preferably an alkyl group having 1 to 6 carbon atoms, more preferably an alkyl group having 1 to 4 carbon atoms; a haloalkyl group, preferably a haloalkyl group having 1 to 2 carbon atoms, more preferably a trihalomethyl group having a fluorine atom, a chlorine atom or a bromine atom; an alkoxy group, preferably an alkoxy group having 1 to 4 carbon atoms; an alkylthio group, preferably an alkylthio group having 1 to 4 carbon atoms; an alkylsulfinyl group, preferably an alkylsulfinyl group having 1 to 4 carbon atoms; an alkylsulfonyl group, preferably an alkylsulfonyl group having 1 to 4 carbon atoms; a cycloalkyl group, preferably a cycloalkyl group having 3 to 6 carbon atoms; a nitro group; or a cyano group; Xs may be the same or different from each other and m represents 0 or an integer of 1 to 3; or two adjacent Xs represent in combination a group represented by the formula: —CH=CH—CH=CH— or

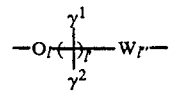

wherein W represents an oxygen atom or a group represented by S(O)$_p$ (wherein p represents 0, 1 or 2; $\gamma^1$ and $\gamma^2$ respectively represent a hydrogen atom or a lower alkyl group, preferably a hydrogen atom or a methyl group; l and l″ respectively represent 0 or 1; l′ represents an integer of 1 to 4 and the sum of l, l′ and l″ is 3 or 4. A represents a group represented by —CH$_2$—, —CH=CH—, —O— or —N(r)— (wherein r represents an alkyl group having 1 to 4 carbon atoms, b represents 0 or 1, preferably 0. R represents an alkyl group, preferably an alkyl group having 1 to 3 carbon atoms; an alkenyl group, preferably an alkenyl group having 3 to 4 carbon atoms, more preferably an allyl group; an alkynyl group, preferably a propargyl group; an alkoxy group, preferably an alkoxy group having 1 to 2 carbon atoms; a fluoroalkyl group, preferably a fluoroalkyl group having 1 to 3 carbon atoms, more preferably fluoroalkyl group having 1 to 2 carbon atoms; or a formyl group. D represents a hydroxyl group. E represents a halogen atom, preferably a chlorine atom, a bromine atom, an iodine atom, more preferably a bromine atom; an alkylsulfonyloxy group, preferably an alkylsulfonyloxy group having 1 to 3 carbon atoms, more preferably a methanesulfonyloxy group; or a benzenesulfonyloxy group which may be substituted by a methyl group, preferably a toluenesulfonyloxy group. Alternatively, D and E represent —O— in combination. V represents a pyridyl group represented by the formula:

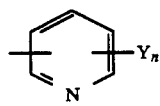

wherein Y represents atom, preferably a chlorine atom or a bromine atom; an alkyl group, preferably an alkyl group having 1 to 4 carbon atoms, more preferably an alkyl group having 1 to 2 carbon atoms, most preferably a methyl group; a haloalkyl group, preferably a haloalkyl group having 1 to 2 carbon atoms, more preferably a trifluromethyl group, a chlorodifluoromethyl group, a dichlorofluoro methyl group, a trichloromethyl group, most preferably a trifluoromethyl group; an alkoxy group, preferably an alkoxy group having 1 to 4 carbon atoms, more preferably an alkoxy group having 1 to 2 carbon atoms, most preferably methoxy group; or a haloalkoxy group, preferably a haloalkoxy group having 1 to 4 carbon atoms, more preferably a haloalkoxy group having 1 to 2 carbon atoms, or a group represented by $S(O)_qT$ (wherein T represents an alkyl group, preferably an alkyl group having 1 to 4 carbon atoms, more preferably an alkyl group having 1 to 2 carbon atoms, most preferably methyl group, or a haloalkyl group, preferably a haloalkyl group having 1 to 2 carbon atoms, and q is 0, 1 or 2, preferably 2, Ys may be the same or different from each other; and n represents 0, 1 or 2.

A compound according to the present invention which is represented by the general formula (I) can be prepared, for example, in accordance with the following reaction scheme:

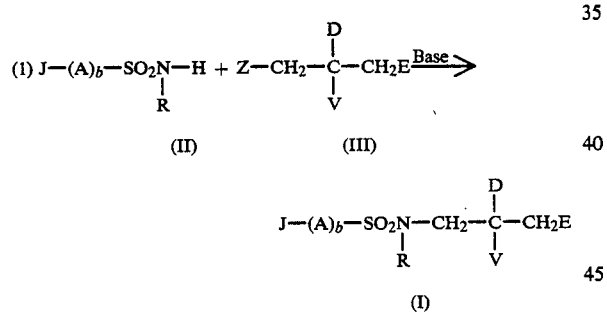

wherein Z represents a halogen atom or a sulfonyloxy group such as a tosyloxy group, and J, A, R, D, E, V and b are the same as defined above.

The above-mentioned reaction is carried out in the presence of an appropriate base without any solvent or in a solvent. As examples of the appropriate solvent, an aprotic solvent such as N,N-dimethylformamide, N-methylpyrrolidone, dimethylsulfoxide, acetonitrile, tetrahydrofuran, dioxane and 1,2-dimethoxyethane may be exemplified. As the base, sodium hydride, potassium hydride, metal sodium, metal potassium, sodium hydroxide, potassium hydroxide, sodium carbonate and potassium carbonate may be exemplified. This reaction is carried out in a temperature range of $-20°$ to $100°$ C., preferably $-10°$ to $60°$ C. for 0.5 to 24 hours, preferably 0.5 to 12 hours.

The reaction represented by the above-described reaction formula may also be carried out in a two-phase system of an aqueous solution of alkali metal hydroxide and an organic solvent in the presence of a phase-transfer catalyst. The phase-transfer catalyst used in the present invention is selected from a wide range, for example, benzyltrialkylammonium halides, tetraalkylammonium halides, methyltrialkylammonium halides, alkyltrimethylammonium halides, alkyltrimethylammonium hydroxides and tetraalkylammonium disulfides. More concretely, the phase-transfer catalyst of benzyltrimethyl-(or ethyl) ammonium chloride (or bromide), tetra n-butylammonium chloride (or bromide, iodide) and methyltrioctyl (or decyl) ammonium chloride may be exemplified. The amount of catalyst to be added is in the range of 1/5 mol equivalent to 1/250 mol equivalent, preferably about 1/50 mol equivalent to 1/100 mol equivalent based on 1 mol equivalent of a sulfonamide represented by the formula (II).

As the aqueous solution of an alkali hydroxide, for example, an aqueous solution of sodium hydroxide and an aqueous solution of potassium hydroxide will be mentioned, and the concentration thereof is preferably 35 to 60%. As the organic solvent, for example, an aprotic solvent such as benzene, toluene, xylene, cyclohexane and cycloheptane may be exemplified.

The reaction temperature is $10°$ to $100°$ C., preferably $40°$ to $80°$ C., and the reaction time is 0.5 to 24 hours, preferably 1 to 12 hours.

$$(2)\ J-(A)_b-SO_2N-CH_2-C=CH_2 \xrightarrow{[O]}$$
$$\quad\quad\quad\quad\quad\quad\quad\quad |\quad\quad\quad\ |$$
$$\quad\quad\quad\quad\quad\quad\quad\quad R\quad\quad\quad V$$

(IV)

$$\quad\quad\quad\quad\quad\quad\quad\quad\quad\quad\quad\quad\quad D^1$$
$$\quad\quad\quad\quad\quad\quad\quad\quad\quad\quad\quad\quad\quad |$$
$$J-(A)_b-SO_2N-CH_2-C-CH_2E^1$$
$$\quad\quad\quad\quad\quad\quad\ |\quad\quad\quad\ |$$
$$\quad\quad\quad\quad\quad\quad\ R\quad\quad\quad V$$

(Ia)

wherein J, A, R, V and b are the same as defined above, and $D^1$ and $E^1$ represent —O— in combination.

The above-described oxidation reaction is carried out in the presence of an oxidizing agent in a solvent such as chloroform, dichloromethane, carbon tetrachloride and water.

As the oxidizing agent, m-chloroperbenzoic acid, peracetic acid, hydrogen peroxide, etc. will be mentioned. These may be used singly, or with a buffer agent such as sodium acetate added thereto in order to prevent a secondary reaction and to stabilize the product. The reaction is ordinarily carried out in a temperature range of $-20°$ to $100°$ C., preferably $10°$ to $70°$ C. for 1 to 24 hours, preferably 2 to 12 hours.

The material compound (IV) is obtained, for example, in accordance with the following reaction scheme (a) and (b):

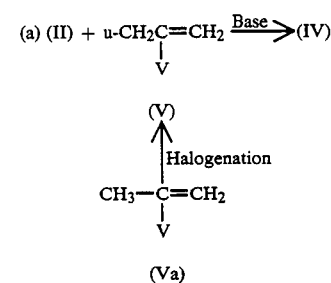

wherein u represents a halogen atom and V is the same as defined above.

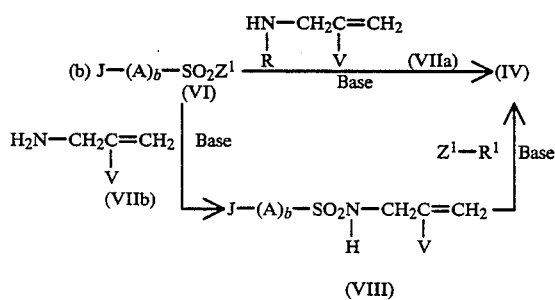

wherein $R^1$ represents the same as R except an alkoxy group and a formyl group, $Z^1$ represents a halogen atom, and J, A, R, V and b are the same as defined above.

The amine derivatives (VIIa) and (VIIb) are obtained, for example, in accordance with the following reaction scheme:

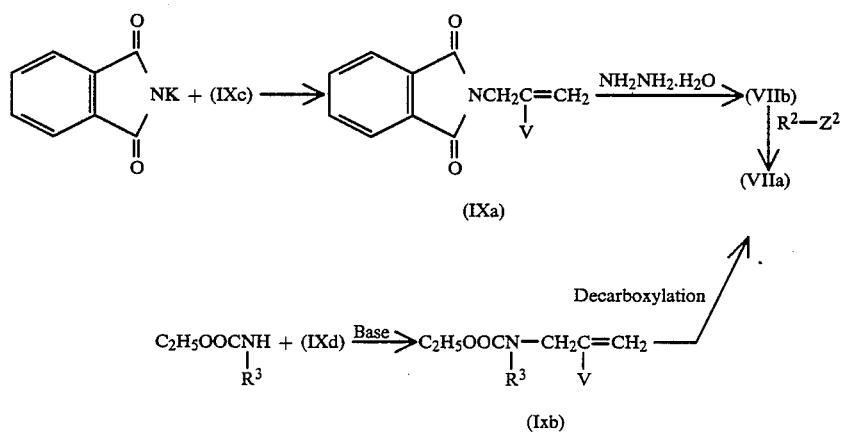

wherein $R^2$ represents the same as R except an alkoxy group; $Z^2$ represents a halogen atom, or when $R^2$ represents a formyl group, $Z^2$ represents a hydroxyl group or a fatty acid residue which constitutes a mixed acid anhydride together with $R^2$; $R^3$ represents an alkoxy group; and V is the same as defined above.

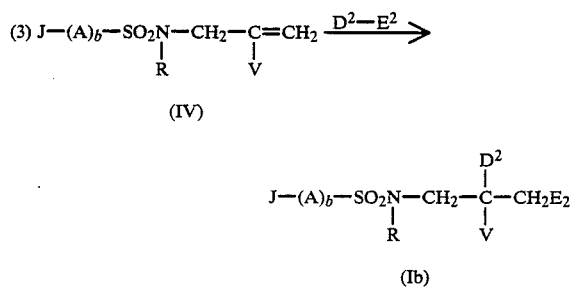

wherein $D^2$ represents a hydroxyl group, $E^2$ a halogen atom, and J, A, R, V and b are the same as defined above.

The above-described reaction is achieved by an addition reaction of a hypohalous acid to a double bond, in other words, by the reaction of forming a halohydrin from an olefin compound. The reaction is preferably carried out by making to act an alkali metal hypohalite, N-halogenosuccinimide, chlorine, bromine, iodine, etc. in water or an aqueous solvent in the presence of or without an acid and/or an oxidizing agent. The reaction temperature is $-30°$ to $100°$ C., preferably $-10°$ to $60°$ C. and the reaction time is 0.1 to 24 hours, ordinarily 0.5 to 6 hours.

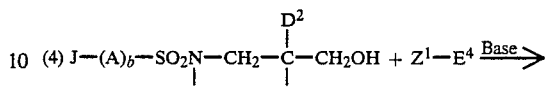

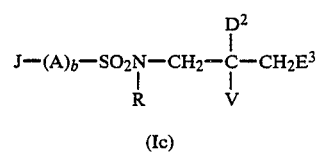

wherein $E^4$ represents an alkylsulfonyl group or a benzenesulfonyl group which may be substituted, $E^3$ represents an alkylsulfonyloxy group or a benzenesulfonyloxy group which may be substituted, and J, A, R, V, $D^2$, $Z^1$ and b are the same as defined above.

The above-described sulfonylation reaction is carried out without any solvent or in a solvent in the presence of an appropriate base. In the case where a solvent is used, N,N-dimethylformamide, N-methylpyrrolidone, tetrahydrofuran, dioxane, 1,2-dimethoxyethane, benzene, toluene, ethyl acetate, methylene chloride and chloroform may be exemplified as an appropriate solvent. As the base, pyridine, triethylamine, N,N-dimethyl (or diethyl) aniline, sodium (or potassium) bicarbonate, sodium (or potassium) carbonate, sodium (or potassium) hydroxide, sodium hydride, etc. may be exemplified. The reaction temperature is $-20°$ C. to $100°$ C., preferably $0°$ to $60°$ C., and the reaction time is ordinarily 1 to 24 hours.

The material compound (X) can be obtained, for example, in accordance with the following reaction scheme:

-continued

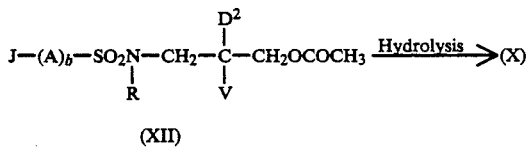

(XII)

wherein J, A, R, $D^2$, V and b are the same as defined above.

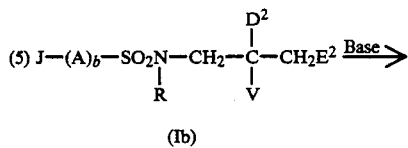

(Ib)

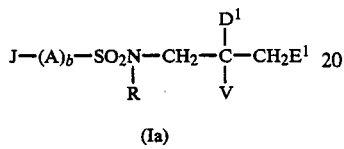

(Ia)

wherein J, A, R, $D^2$, $E^2$, V, $D^1$, $E^1$ and b are the same as defined above.

The above-described reaction is carried out in a solvent such as methanol, ethanol, 2-propanol, acetone, ethylmethylketone, ether, tetrahydrofuran, dioxane, benzene, toluene, ethyl acetate, N,N-dimethylformamide, dimethylsulfoxid, N-methylpyrrolidone, acetonitrile and water and a mixed solvent thereof in the presence of a base such as sodium (or potassium) bicarbonate, sodium (or potassium) carbonate, sodium (or potassium) hydroxide, sodium hydride, sodium alcoholate, pyridine, triethylamine and N,N-dimethyl (or diethyl) aniline at a temperature of −10° to 120° C., preferably 0° to 80° C. The reaction time is ordinarily 0.1 to 12 hours.

There are optical isomers in a compound obtained in the above-described way. These isomers are usually obtained in the form of a racemate, but it is possible to obtain an enantiomer by known methods such as asymmetric synthesis. The compound of the present invention is usable either in the form of a racemate or each isomer.

When the compound of the present invention is applied to a herbicide, such compound may be used as it is, or in the form of a wettable powder, a granules, an emulsifiable concentrate or a suspension concentrate produced by an ordinary method using a herbicidally acceptable carrier, surfactant or the like. As the carrier and surfactant, for example, those described in Japanese Patent Application Laid-Open (KOKAI) No. 60-25986 (1985) are usable. It is possible to use a herbicide containing a compound of the present invention by mixing it with another agricultural chemical used in the same field, e.g., an insecticide, fungicide, herbicide, growth regulating agent, and a fertilizer.

The amount of herbicide used is different depending upon the kind of the compound used, weed being treated, treating time, treating method and the nature of the soil, but ordinarily, the preferable amount is 0.25 to 40 g per are, preferably 1 to 20 g per as an active ingredient.

A slight change is observed in the biological activity of a compound of the present invention in accordance with the kind of a modified functional group and the position of substitution, but any compound of the present invention has a very strong herbicidal activity on Echinochloa crus-galli, which is the most harmful weed to paddy-rice plants, from before the germination to an advanced stage of growing, and causes little damage to paddy-rice plants.

The herbicidal spectrum of a compound of the present invention is the highest to Echinochloa crus-galli. A compound of the present invention is also effective to weeds of Cyperaceae such as *Cyperus difformis, Scripus juncoides* and *Eleocharis acicularis* and annual broadleaf weeds such as *Rotala indica* and *Monochoria vaginalis,* and also has a high sensitivity to *Cyperus serotinus,* which is a strongly noxious perennial weed.

A compound of the present invention is effective in a low dosage as a herbicidal active ingredient to various kinds of weeds from before the germination to an advanced stage of growing, and has a wide range of adaptible time in which the compound is preferably used. In addition, a compound of the present invention has a treating activity on not only the soil of flooded field but also the soil of farmland.

The activity of a compound of the present invention on annual broadleaf weeds and perennial broadleaf weeds such as Sagittaria pygmaea in an advanced growing stage is slightly low, but by mixing the compound with a herbicide which is effective to these weeds, it is possible to greatly enlarge the width of the herbicidal spectrum and to stabilize the herbicidal effect. The mixing ratio (by dosage) thereof is 0.005 to 100 g/are, preferably 0.01 to 50 g/are.

In this case, the followings may be exemplified as preferred herbicides mixed with a compound of the present invention:

Pyrazole herbicide:
4-(2,4-dichlorobenzoyl)-1,3-dimethylpyrazol-5-yl p-toluenesulfonate, 4-(2,4-dichlorobenzoyl)-1,3-dimethyl-5-phenacyloxypyrazole, 4-(2,4-dichloro-3-methylbenzoyl)-1,3-dimethyl-5-(4-methylphenacyloxy)pyrazole, 4-(2,4-dichlorobenzoyl)-1-methyl-5-phenacyloxypyrazole.

Sulfonylurea herbicide:
methyl 2-(4,6-dimethoxypyrimidin-2-ylcarbamoylaminosulphonylmethyl)benzoate, ethyl 5-(4,6-dimethoxypyrimidin-2-ylcarbamoylaminosulphonyl)-1-methylpyrazole-4-carboxylate.

Phenoxy herbicide:
2,4-dichlorophenoxyacetic acid and a derivative thereof, 4-chloro-2-methylphenoxyacetic acid and a derivative thereof, 4-(4-chloro-2-methylphenoxy)-butyric acid and a derivative thereof, S-ethyl 4-chloro-2-methylphenoxythioacetate, 2-(2-naphthoxy)propionanilide, 2-(2,4-dichloro-3-methylphenoxy)propionanilide, butyl 2-[4-(5-trifluoromethyl-2-pyridyloxy)phenoxy]propionate.

Haloacetoanilide herbicide:
2-chloro-2',6'-diethyl-N-butoxymethylacetoanilide, 2-chloro-2',6'-diethyl-N-propoxyethylacetoanilide, ethyl N-chloroacetyl-N-(2,6-diethylphenyl)aminoacetate.

Acid amide herbicide:
3',4'-dichloropropionanilide, 2', 3'-dichloro-4-ethoxymethoxybenzanilide, 2-bromo-3,3-dimethyl-N-(α,α-dimethylbenzyl)butanamide, 2-benzothiazol-2-yloxy N-methylacetanilide, 2',4'-difluoro-2-(3-trifluoromethylphenoxy)nicotinic acid amide.

Carbamate herbicide:

S-(4-chlorobenzyl)-N,N-diethylthiolcarbamate, S-ethyl-N,N-hexamethylenethiolcarbamate, N,N-hexamethylene-S-isopropylthiolcarbamate, S-benzyl-N-ethyl-N-(1,2-dimethylpropyl)thiolcarbamate, S-(1-methyl-1-phenethyl)-piperidine-1-carbothioate, O-(3-t-butylphenyl)-N-(6-methoxypyridine-2-yl)-N-methylthiocarbamate Urea herbicide:
1-(α,α-dimethylbenzyl)-3-(4-methylphenyl)urea, 3-(benzothiazol-2-yl)-1,3-dimethylurea, 3-(3,4-dichlorophenyl)-1-methoxy-1-methylurea, 3-(3,4-dichlorophenyl)-1,1-dimethylurea, 3-[4-(4-methylphenetyloxy)-phenyl]-1-methoxy-1-methylurea, 1-(2-substituted benzyl)-3-(α,α-dimethylbenzyl)urea.

Diphenylether herbicide:
2,4,6-trichloro-4'-nitrodiphenyl ether, 2,4-dichloro-3'-methoxy-4'-nitrodiphenyl ether, methyl 5-(2,4-dichlorophenoxy)-2-nitrobenzoate, 3-[5-(2-chloro-4-trifluoromethylphenoxy)-2-nitrophenoxy]tetrahydrofuran.

Triazine herbicide:
2-chloro-4-ethylamino-6-isopropylamino-1,3,5-triazine, 2,4-bis(ethylamino)-6-methylthio-1,3,5-triazine, 2-ethylamino-4-(1,2-dimethylpropylamino)-6-methylthio-1,3,5-triazine, 2,4-bis(isopropylamino)-6-methylthio-1,3,5-triazine, 4-amino-6-t-butyl-3-methylthio-1,2,4-triazine- b 5-(4H)-one.

Dinitroaniline herbicide:
2,6-dinitro-N,N-dipropyl-4-trifluoromethylaniline, N-(1-ethylpropyl)-3,4-dimethyl-2,6-dinitroaniline, 3,5-dinitro-N,N-dipropylsulfanilamide.

Nitrile herbicide:
4-hydroxy-3,5-diiodobenzonitrile, 3,5-dibromo-4-hydroxybenzonitrile, 2,6-dichlorobenzonitrile.

Phosphorous-containing herbicide:
O-ethyl-O-(5-methyl-2-nitrophenyl)-N-sec-butylphosphoroamidate, S-(2-benzenesulfonylaminoethyl)-O,O-diisopropylphosphorodithioate, S-(2-methylpiperidin-1-yl)carbonylmethyl-O,O-dipropylphosphorodithioate, N-(phosphonomethyl)glycine, ammonium (3-amino-3-carboxy)propylmethylphosphinate, sodium (2-amino-4-methylphosphino)butyrylalanylalaninate.

Quaternary ammonium salt herbicide:
1,1'ethylene-2,2'-pipyridylium dibromide, 1,1'-dimethyl-4,4'-bipyridylium dichloride.

Other herbicides:
3,6-dichloro-2-methoxybenzoic acid, 3,7-dichloroquinoline-8-carboxylic acid, pentachlorophenol, 2-sec-butyl-4,6-dinitrophenol, 2-amino-3-chloro-1,4-naphthoquinone, 1,2-dihydropyridazine-3,6-dione, 3-(2-methylphenoxy)pyridazine, 3-isopropyl-1H-2,1,3-benzothiazin-4(3H)-one 2,2-dioxide, 2,2-dichloropropionic acid, 2,2,3,3-tetrafluoropropionic acid, methyl 6-(4-isopropyl-4-methyl-5-oxo-2-imidazolin-2-yl)-3(4)methylbenzoate, 2-(4-isopropyl-4-methyl-5-oxo-2-imidazolin-2-yl)nicotinic acid and a salt thereof, 2-(4-isopropyl-4-methyl-5-oxo-2-imidazolin-2-yl)quinoline-3-carboxylic acid, 1-methyl-4-(1-methylethyl)-2-(2-methylphenylmethoxy)-7-oxabicyclo-[2,2,1]heptane, 1-(3-methylphenyl)-5-phenyl-1H-1,2,4-triazole-3-carboxamide, 2-(N-ethoxybutylimidoyl)-5-(2-ethylthiopropyl)-3-hydroxy-2-cyclohexene-1-one, 2-(3,5-dichlorophenyl)-2-(2,2,2-trichloroethyl)oxirane, N-[4-(4-chlorbenzyloxy)-phenyl]-3,4,5,6-tetrahydrophthalimide, N-(4-chloro-2-fluoro-5-propargyloxyphenyl)-3,4,5,6-tetrahydrophthalimide, 3-(2,4-dichloro-5-isopropoxyphenyl)-5-t-butyl-1,3,4-oxadiazol-2(3H)-one, 4-methoxy-3,3'-dimethylbenzophenone, 2-ethoxy-2,3-dihydro-3,3-dimethyl-5-benzofuranyl methane sulfonate, 1-methyl-3-phenyl-5-(3-trifluoromethylphenyl)-pyridine-4(1H)-one, S,S-dimethyl 2-(difluoromethyl) 4-(2-methylpropyl)-6-(trifluoromethyl)-3,5-pyridinedicarbothioate.

These may be used in the form of a mixture.

As other aspect of the present invention, the heart of the present invention lies in a 1-(halogenomethyl)vinyl-pyridine represented by the following general formula (V):

$$u\text{-}CH_2\text{---}C\text{=}CH_2 \qquad \text{(V)}$$
$$|$$
$$\overset{\circ}{V}$$

(wherein u represents a halogen atom and $\overset{\circ}{V}$ a pyridyl group which may be substituted), which is useful as an intermediate of an N-[2-(pyridyl)propyl]-N-substituted sulfonamide represented by the general formula (I).

In the general formula (V), V preferably represents a pyridyl group represented by the formula:

[structure: pyridine ring with $Y_n$ substituent]

wherein Y represents a halogen atom, preferably a fluorine atom, a chlorine atom, and a bromine atom, more preferably a chlorine atom and a bromine atom; a haloalkyl group, preferably a haloalkyl group having 1 to 2 carbon atoms, more preferably a trifluoromethyl group, a chlorodifluoromethyl group, a dichlorofluoromethyl group, a trichloromethyl group, particularly preferably a trifluoromethyl group; an alkyl group, preferably an alkyl group having 1 to 4 carbon atoms, more preferably an alkyl group having 1 to 2 carbon atoms, particularly preferably a methyl group; an alkoxy group, preferably an alkoxy group having 1 to 4 carbon atoms, more preferably an alkoxy group having 1 to 2 carbon atoms, particularly preferably a methoxy group; a haloalkoxy group, preferably a haloalkoxy group having 1 to 2 carbon atoms, more preferably a trifluoromethoxy group and a difluoromethoxy group; a group represented by $S(O)_qT$ wherein q represents 0, 1 or 2, preferably 0 and T represents an alkyl group having 1 to 4 carbon atoms, preferably an alkyl group having 1 to 2 carbon atoms, more preferably a methyl group, or a haloalkyl group, preferably a haloalkyl group having 1 to 2 carbon atoms, and n represents 0 or an integer of 1 to 4, preferably 0, 1 or 2. When n is an integer of 2 to 4, Ys may be the same or different from each other.

u represents a halogen atom, preferably a fluorine atom, a chlorine atom, a bromine atom or an iodine atom, more preferably a chlorine atom, a bromine atom or an iodine atom.

A compound according to the present invention which is represented by the general formula (V) can be prepared, for example, in accordance with the following reaction formulae (1) and (2):

$$(1) \quad CH_3\text{---}C\text{=}CH_2 \xrightarrow{\text{Halogenation}} u\text{-}CH_2\text{---}C\text{=}CH_2$$
$$\qquad\qquad |\qquad\qquad\qquad\qquad\qquad\qquad |$$
$$\qquad\qquad V\qquad\qquad\qquad\qquad\qquad\qquad V$$
$$\qquad\quad (III')\qquad\qquad\qquad\qquad\qquad\quad (V)$$

wherein V and u are the same as defined above.

This reaction is a reaction distinguished as a halogenation reaction at an allyllic position in organic synthetic chemistry. The halogenation reaction at an allylic position represented by the general formula (III') is achieved by reacting an allyl compound with an appropriate halogenating agent in the presence of heat and/or a free radical initiator (e.g., light, a peroxide and an azo compound), as occasion demands, in accordance with a method described by H. O. House, Modern Synthetic Reactions 2nd Ed. pp. 478–491 (1972), published by W. A. Benjamin, Inc.

As a similar reaction and, in particular, as a halogenation reaction at an allyllic position of propenes having an aryl group at 2-position, bromination of α-methylstyrene is described by S. F. Reed Jr., J. Org. Chem., 30 3258 (1965). It is described therein that in this case, a substantially equivalent of a by-product is produced together with the objective substance.

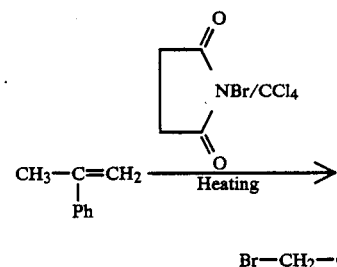

Br—CH$_2$—C=CH$_2$ + CH$_3$—C=CHBr
    |                  |
    Ph                 Ph

T. Hori & K. B. Sharpless, J. Org. Chem. 44 4204 (1979) disclose non-radical chlorization reaction of α-methylstyrene using an aryl selenium derivative or N-sulfinyl-p-toluenesulfonamide as a catalyst.

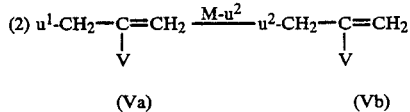

(Va)                    (Vb)

wherein $u^1$ represents a chlorine atom or a bromine atom, $u^2$ represents a fluorine atom, a bromine atom or an iodine atom, M represents an alkali metal cation, and V is the same as defined above, provided that $u^1 \neq u^2$.

The above-described halogen exchange reaction is carried out by reacting an alkali metal halide such as sodium (or potassium) iodide, sodium (or potassium) bromide and potassium (or cesium) fluoride in a solvent such as acetonitrile, acetone, ethylmethylketone, ethyl acetate, benzene, toluene, tetrahydrofuran, dioxane, 1,2-dimethoxyethane, N,N-dimethylformamide, N-methylpyrrolidone, dimethylsulfoxide and sulfolane in the presence or absence of a crown ether.

As a compound represented by the general formula (V), 3 (or 4)-(1-halogenomethylvinyl)pyridine, 2-chloro(bromo or fluoro)-6-(1-halogenomethylvinyl)-4-methoxypyridine, 4-(1-halogenomethylvinyl)-2-trifluoromethyl (trichloromethyl, dichlorofluoromethyl or chlorodifluoromethyl)pyridine, 2-(1-halogenomethylvinyl)-6-methylsulfinyl (or methylsulfonyl)pyridine, 3-chloro (or bromo)-5-(1-halogenomethylvinyl)-2-fluoropyridine, 2-ethyl (ethoxy, ethylthio, isopropyl or isopropoxy)-6-(1-halogenomethylvinyl)pyridine, 2,4-dichloro (or dibromo)-6-(1-halogenomethylvinyl)pyridine, 4-chloro (or fluoro)-6-(1-halogenomethylvinyl)-2-trifluoromethylpyridine, 3-chloro-5-(1-halogenomethylvinyl)pyridine, 2-chloro (or bromo)-4-(1-halogenomethylvinyl)pyridine, 2-chloro (or bromo)-4-(1-halogenomethylvinyl)-6-methoxypyridine. The term "halogeno" in the above-described compounds represents "chloro", "bromo" or "iodo".

A compound represented by the general formula (V) is a useful compound as an intermediate of the N-[2-(pyridyl)propyl]-N-substituted sulfonamide represented by the formula (I).

The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the invention to adapt it to various usages and conditions.

I. Synthesis of (1-halogenomethylvinyl)pyridine

EXAMPLE I-1

Preparation of 2-(1-chloromethylvinyl)pyridine (Compound No. I-1)

A mixture of 4.0 g of 2-isopropenylpyridine, 4.5 g of N-chlorosuccinimide and 8 ml of carbon tetrachloride was stirred at 150° to 160° C. for 20 minutes. After the reaction mixture was cooled to room temperature, n-hexane was added thereto to remove the insoluble matter through filtration. After distilling off the solvent, the residue was purified by silica gel column chromatography (eluted with n-hexane-ethyl acetate 20:1) to obtain 1.0 g of the objective compound.

$n_D^{25}$ 1.5541

IR spectrum (neat) cm$^{-1}$: 1585, 1565, 1465, 1430, 1260, 1045, 990, 925.

'H-NMR spectrum (CCl$_4$-TMS)$^\delta$: 4.60 (2H, s), 5.67 (1H, s), 5.91 (1H, s), 7.1 to 7.25 (1H, m), 7.4–7.8 (2H, m), 8.57 (1H, dd).

EXAMPLE I-2

Preparation of 4-chloro-2-(1-chloromethylvinyl)pyridine (Compound No. I-2)

A mixture of 4.3 g of 4-chloro-2-isopropenylpyridine, 3.8 g of N-chlorosuccinimide and 10 ml of carbon tetrachloride was stirred in an oil bath at 150° to 160° C. for hour. After the reaction mixture was cooled to room temperature, n-hexane was added thereto to remove the insoluble matter through filtration. After distilling off the solvent, the residue was purified by silica gel column chromatography (eluted with n-hexane-ethyl acetate 20:1) to obtain 0.90 g of the objective compound.

$n_D^{25}$ 1.5711

IR spectrum (neat) cm$^{-1}$: 1570, 1550, 1460, 1395, 925, 825.

'H-NMR spectrum (CCl$_4$-TMS)$^\delta$: 4.60 (2H, s), 5.73 (1H, s), 5.97 (1H, s), 7.22 (1H, dd), 7.58 (1H, d), 8.50 (1H, d).

EXAMPLE I-3

Preparation of 2-chloro-6-(1-chloromethylvinyl)pyridine (Compound No. I-3)

A mixture of 29.8 g of 2-chloro-6-isopropenylpyridine, 29.8 g of N-chlorosuccinimide and 60 ml of benzene was stirred at 80° C. for 5 hours. After the reaction mixture was cooled to room temperature, 200 ml of n-hexane was added thereto to remove the insoluble matter through filtration. After distilling off the solvent, the residue was purified by silica gel column chromatography (eluted with n-hexane then n-hexane - ethyl acetate 20:1) to obtain 20.6 g of the objective compound.

$n_D^{25}$ 1.5747

IR spectrum (neat) cm$^{-1}$: 1580, 1555, 1440, 1405, 1160, 1135, 930, 805.

'H-NMR spectrum (CCl$_4$-TMS)$^\delta$: 4.60 (2H, s), 5.73 (1H, s), 6.06 (1H, s), 7.26 (1H, d), 7.48 (1H, d), 7.66 (1H, dd).

EXAMPLE I-4

Preparation of 2-(1-bromomethylvinyl)-6-chloropyridine (Compound No. I-4)

A mixture of 1.0 g of 2-chloro-6-(1-chloromethylvinyl) pyridine, 2.0 g of potassium bromide, 5 ml of 2-butanone and 5 ml of N,N-dimethylformamide was stirred at 100° C. for 12 hours. After the reaction mixture was cooled to room temperature, water was added thereto to extract the mixture with ethyl acetate. The extract was subsequently washed with an aqueous solution of 10% sodium thiosulfate, water, saturated saline solution in that order, and dried over anhydrous magnesium sulfate. After distilling off the solvent, the residue was purified by silica gel column chromatography (eluted with n-hexane - ethyl acetate 25:1) to obtain 0.80 g of the objective compound.

$n_D^{25}$ 1.5938

IR spectrum (neat) cm$^{-1}$: 1580, 1555, 1440, 1410, 1160, 1135, 985, 805.

'H-NMR spectrum (CCl$_4$-TMS)$^\delta$: 4.43 (2H, s), 5.70 (1H, s), 6.02 (1H, s), 7.24 (1H, d), 7.48 (1H, d), 7.67 (1H, dd).

EXAMPLE I-5

Preparation of 2-chloro-6-(1-iodomethylvinyl)pyridine (Compound No. I-5)

A mixture of 0.50 g of 2-chloro-6-(1-chloromethylvinyl) pyridine, 0.88 g of potassium iodide, 5 ml of acetone and 0.5 ml of N,N-dimethylformamide was stirred at 50° to 60° C. for 5 hours. After the reaction mixture was cooled to room temperature, water was added thereto to extract the mixture with ethyl acetate. The extract was subsequently washed with an aqueous solution of 10% sodium thiosulfate, water, saturated saline solution in that order, and dried over anhydrous magnesium sulfate. After distilling off the solvent, the residue was purified by silica gel column chromatography (eluted with dichloromethane) to obtain 0.45 g of the objective compound.

$n_D^{25}$ 1.6250

IR spectrum (neat) cm$^{-1}$: 1580, 1555, 1440, 1410, 1160, 1135, 985, 800.

'H-NMR spectrum (CCl$_4$-TMS)$^\delta$: 4.38 (2H, s), 5.70 (1H, s), 5.89 (1H, s), 7.22 (1H, d), 7.42 (1H, d), 7.62 (1H, dd).

EXAMPLE I-6

Preparation of 2-bromo-6-(1-chloromethylvinyl)pyridine (Compound No. I-6)

A mixture of 3.60 g of 2-bromo-6-isopropenylpyridine, 2.91 g of N-chlorosuccinimide and 8 ml of benzene was stirred at 80° C. for 5 hours. After the reaction mixture was cooled to room temperature, n-hexane was added thereto to remove the insoluble matter through filtration. After distilling off the solvent, the residue was purified by silica gel column chromatography (eluted with n-hexane then n-hexane - ethyl acetate 20:1) to obtain 1.50 g of the objective compound.

$n_D^{25}$ 1.5952

IR spectrum (neat) cm$^{-1}$: 1580, 1550, 1435, 1160, 1125, 1115, 800.

'H-NMR spectrum (CCl$_4$-TMS)$^\delta$: 4.56 (2H, s), 5.71 (1H, s), 6.04 (1H, s), 7.3 to 7.6 (3H, m).

EXAMPLE I-7

Preparation of 3-bromo-5-(1-chloromethylvinyl)pyridine (Compound No. I-7)

A mixture of 7.12 g of 3-bromo-5-isopropenylpyridine, 6.85 g of N-chlorosuccinimide and 15 ml of carbon tetrachloride was stirred at 80° C. for 7 hours. After the reaction mixture was cooled to room temperature, the insoluble matter was filtered out. The filtrate was concentrated under a reduced pressure and the residue was purified by silica gel column chromatography (eluted with ethyl acetate-n-hexane 1:19) to obtain 2.23 g of the objective compound.

$n_D^{25}$ 1.5929

IR spectrum (neat) cm$^{-1}$: 1440, 1,415, 1290, 1020, 920, 885, 810, 750.

'H-NMR spectrum (CDCl$_3$-TMS)$^\delta$: 4.47 (2H, s), 5.65 and 5.66 (1H, s, each), 7.96 (1H, dd), 8.69 (1H, br.s).

EXAMPLE I-8

Preparation of 2-(1-chloromethylvinyl)-6-methylpyridine (Compound No. I-8)

A mixture of 4.7 g of 2-isopropenyl-6-methylpyridine, 4.7 g of N-chlorosuccinimide and 10 ml of carbon tetrachloride was stirred at 150° to 160° C. for 30 minutes. After the reaction mixture was cooled to room temperature, n-hexane was added thereto to remove the insoluble matter through filtration. After distilling off the solvent, the residue was purified by silica gel column chromatography (eluted with n-hexane-ethyl acetate 20:1). to obtain 2.0 g of the objective compound.

$n_D^{25}$ 1.5437

IR spectrum (neat) cm$^{-1}$: 1580, 1570, 1460, 1260, 930, 805.

'H-NMR spectrum (CCl$_4$-TMS)$^\delta$: 2.53 (3H, s), 4.61 (2H, s), 5.64 (1H, s), 5.92 (1H, s), 7.03 (1H, d), 7.53 (1H, dd).

EXAMPLE I-9

Preparation of 2-(1-chloromethylvinyl)-6-trifluoromethylpyridine (Compound No. I-9)

A mixture of 11.0 g of 2-isopropenyl-6-trifluoromethylpyridine, 8.7 g of N-chlorosuccinimide and 25 ml of benzene was stirred at 80° C. for 7 hours. After the reaction mixture was cooled to room temperature, 50 ml of n-hexane was added thereto to remove the insoluble matter through filtration. After distilling off the solvent, the residue was purified by silica gel column chromatography (eluted with n-hexane then n-hexane-ethyl acetate 20:1) to obtain 5.5 g of the objective compound.

$n_D^{25}$ 1.4846

IR spectrum (neat) cm$^{-1}$: 1590, 1340, 1320, 1195, 1135, 825.

'H-NMR spectrum (CCl$_4$-TMS)$^\delta$: 4.70 (2H, s), 587 (1H, s), 6.14 (1H, s), 7.5 to 8.0 (3H, m).

EXAMPLE I-10

Preparation of 2-(1-chloromethylvinyl)-6-methoxypyridine (Compound No. I-10)

A mixture of 13.6 g of 2-isopropenyl-6-methoxypyridine, 16.3 g of N-chlorosuccinimide, 0.2 g of t-butylhydroperoxide and 30 ml of carbon tetrachloride was stirred at 140° C. for 5 hours while being irradiated with light. After the reaction mixture was cooled to room temperature, the insoluble matter was filtered out. The filtrate was concentrated under a reduced pressure and the residue was purified by silica gel column chromatography (eluted with ethyl acetate-n-hexane 1:25) to obtain the following three fractions: 4.75 g of a first fraction (objective product/byproduct=0.2), 5.99 g of a second fraction (objective product/byproduct=0.714) and 0.41 g of a third fraction (objective product=1.0).

$n_D^{25}$ 1.5484

IR spectrum (neat) cm$^{-1}$: 1580, 1465, 1260, 1025, 805, 750.

'H-NMR spectrum (CCl$_4$-TMS)$^\delta$: 3.93 (3H, s), 4.55 (2H, s), 5.59 and 5.99 (1H, obs.s, each), 6.62 (1H, d), 7.10 (1H, d), 7.53 (1H, t).

The mixture ratio of the objective product and byproduct was based on the integrated value in the 'H-NMR spectrum.

Separation of byproduct and the structure thereof

Reaction was carried out under the same conditions as in Example I-10, and thereafter the concentrated filtrate was purified by silica gel column chromatography (eluted with ethyl acetate - n-hexane 1:40) to obtain 1.73 g of a first fraction (byproduct=1.0) and 6.36 g of a second fraction (objective product/byproduct=0.64). It was identified from the following data that the byproduct was 2-(2-chloro-1-methylvinyl)-6-methoxypyridine.

$n_D^{25}$ 1.5535

IR spectrum (neat) cm$^{-1}$: 1620, 1575, 1460, 1430, 1410, 1325, 1260, 1150, 1025, 1000, 790, 730.

'H-NMR spectrum (CCl$_4$-TMS)$^\delta$: 2.28 (3H, d), 3.90 (3H, s), 6.56 (1H, d), 6.85 (1H, d), 7.11 (1H, q), 7.47 (1H, t).

EXAMPLE I-11

Preparation of 2-(1-chloromethylvinyl)-6-methylthiopyridine (Compound No. I-11)

A mixture of 14.5 g of 2-isopropenyl-6-methylthiopyridine, 12.9 g of N-chlorosuccinimide and 30 ml of benzene was stirred at 80° C. for 1 hour. After the reaction mixture was cooled to room temperature, n-hexane was added thereto to remove the insoluble matter through filtration. After distilling off the solvent, the residue was purified by silica gel column chromatography (eluted with n-hexane then n-hexane - ethyl acetate 20:1) to obtain 4.3 g of the objective compound.

$n_D^{25}$ 1.6102

IR spectrum (neat) cm$^{-1}$: 1560, 1435, 1155, 1145, 800, 750.

'H-NMR spectrum (CCl$_4$-TMS)$^\delta$: 2.56 (3H, s), 4.60 (2H, s), 5.65 (1H, s), 5.99 (1H, s), 7.06 (1H, d), 7.20 (1H, d), 7.43 (1H, dd).

EXAMPLE I-12

Preparation of 4-(1-chloromethylvinyl)-2,6-dichloropyridine (Compound No. I-12)

A mixture of 26.3 g of 2,6-dichloro-4-isopropenylpyridine, 33.4 g of N-chlorosuccinimide, 2 g of t-butylhydroperoxide and 30 ml of carbon tetrachrolide was stirred at 180° C. for 5 hours while being irradiated with light. After the reaction mixture was cooled to room temperature, the insoluble matter was filtered out. The filtrate was concentrated under a reduced pressure and the residue was purified by silica gel column chromatography (eluted with ethyl acetate-n-hexane 1:20) to obtain 9.86 g of the objective compound.

$n_D^{25}$ 1.5891

IR spectrum (neat) cm$^{-1}$: 1580, 1530, 1365, 1175, 850, 810, 750.

'H-NMR spectrum (CCl$_4$-TMS)$^\delta$: 4.37 (2H, s), 5.70 and 5.77 (1H, obs.s, each), 7.30 (2H, s).

II. Synthesis of N-[2-(pyridyl)propyl]-N-substituted sulfonamide

EXAMPLE II-1

Preparation of 2-(6-chloropyridine-2-yl)-1,2-epoxy-3-[N-methyl-N-(4-methylthiobenzenesulfonyl)amino]propane To a mixture of 1.0 g of N-methyl-4-methylthiobenzenesulfonylamide and 10 ml of 1,2-dimethoxyethane, 0.28 g of 60% sodium hydride dispersed in oil was added under stirring. After the thus-obtained mixture was stirred at room temperature for 10 minutes, a mixture of 1.13 g of 2-chloro-6-(2-chloromethyloxiran-2-yl)pyridine and 5 ml of 1,2-dimethoxyethane was added thereto and the whole mixture was stirred at 80° to 90° C. for 5 hours. After the reaction mixture was cooled to room temperature, the insoluble content was filtered out and the filtrate was concentrated under a reduced pressure. The residue was purified by silica gel column chromatography (eluted with benzene-ethyl acetate 20:1) to obtain 0.39 g of Compound No. 38 in Table 1.

IR spectrum (KBr) cm$^{-1}$: 1583, 1337, 1160, 1100, 1073.

'H-NMR spectrum (CDCl$_3$-TMS)$^\delta$: 2.53 (3H, s), 2.83 (3H, s), 2.86 (1H, d), 3.23 (1H, d), 3.78 (1H, d), 3.85 (1H, d), 7.2 to 7.8 (7H, m).

EXAMPLE II-2

Preparation of 2-(6-chloropyridine-2-yl)-1,2-epoxy-3-[N-methyl-N-(3-methyl-4-methylthiobenzenesulfonyl)amino]propane To a mixture of 0.60 g of N-methyl-3-methyl-4-methylthiobenzenesulfonylamide, 0.58 g of 2-chloro-6-(2-chloromethyloxiran-2-yl)pyridine, 0.03 g of tetra-n-butylammonium bromide and 6 ml of benzene, 1.1 g of an aqueous solution of 40% sodium hydroxide was added and the whole mixture was stirred at 80° C. for 5 hours. After the reaction mixture was cooled to room temperature, it was subsequently washed with water and brine, and then dried over anhydrous magnesium sulfate. After the solvent was distilled off, the residue was purified by silica gel column chromatography (eluted with benzene-ethyl acetate 15:1) to obtain 0.50 g of Compound No. 65 in Table 1.

IR spectrum (KBr) cm$^{-1}$: 1583, 1337, 1200, 1055.

'H-NMR spectrum (CDCl$_3$-TMS)$^\delta$: 2.36 (3H, s), 2.53 (3H, s), 2.82 (3H, s), 2.86 (1H, d), 3.25 (1H, d), 3.80 (2H, s), 7.2 to 7.8 (6H, m).

EXAMPLE II-3

Preparation of 2-(6-chloropyridin-2-yl)-1,2-epoxy-3-[N-methyl-N-(6-thiachromansulfonyl)amino]propane To a mixture of 0.35 g of N-methyl-6-thiachromansulfonamide, 0.35 g of 2-chloro-6-(2-chloromethyloxiran-2-yl)pyridine, 0.01 g of tetra-n-butylammonium bromide and 5 ml of toluene, 0.8 g of an aqueous solution of 50% sodium hydroxide was added and the whole mixture was refluxed by heating for 2 hours under stirring. After the separation of the water layer, the organic layer was washed with brine and dried over anhydrous magnesium sulfate. After the solvent was distilled off, the residue was purified by silica gel column chromatography (eluted with ethyl acetate-n-hexane 1:4→1:1) to obtain 0.55 g of Compound No. 98 in Table 1.

IR spectrum (KBr) cm$^{-1}$: 1580, 1560, 1450, 1340, 1155, 895, 800.

'H-NMR spectrum (CDCl$_3$-TMS)$^\delta$: 2.01 to 2.27 (2H, m), 2.83 (3H, s), 2.83 to 2.97 (2H, m), 2.89, 3.24 (1H, d, each), 3.01 to 3.14 (2H, m), 3.70, 3.89 (1H, d, each), 7.15 to 7.60 (5H, m), 7.66 (1H, obs.t).

EXAMPLE II-4

Preparation of 1-[N-(4-chlorobenzenesulfonyl)-N-methylamino]-2-(6-chloropyridin-2-yl)-2,3-epoxypropane A mixture of 1.5 g of 3-[N-(4-chlorobenzenesulfonyl)-N-methylamino]-2-(6-chloropyridin-2-yl)propene, 1.0 g of 70% m-chloroperbenzoic acid and 30 ml of chloroform was stirred at 60° C. for 5 hours. After the reaction mixture was cooled to room temperature, 30 ml of carbon tetrachrolide was added thereto, and the whole mixture was subsequently washed with a 2N aqueous solution of sodium hydroxide, an aqueous solution of 10% sodium bisulfite, a 2N aqueous solution of sodium hydroxide, water and brine in that order and dried over anhydrous magnesium sulfate. After the solvent was distilled off, the residue was purified by silica gel column chromatography (eluted with benzene-ethyl acetate 15:1) to obtain 1.1 g of Compound No. 16 in Table 1.

IR spectrum (KBr) cm$^{-1}$: 1582, 1473, 1445, 1340, 1156, 1081.

'H-NMR spectrum (CDCl$_3$-TMS)$^\delta$: 2.83 (3H, s), 2.85 (1H, d), 3.20 (1H, d), 3.77 (1H, d), 3.90 (1H, d), 7.2 to 7.8 (7H, m).

EXAMPLE II-5

Preparation of 1,2-epoxy-3-(N-methyl-N-styrylsulfonylamino)-2-(6-trifluoromethylpyridin-2-yl)propane A mixture of 1.1 g of 3-(N-methyl-N-styrylsulfonylamino)-2-(6-trifluoromethylpyridin-2-yl)propene, 0.20 g of sodium acetate trihydrate, 2.19 g of 40% peracetic acid and 11 ml of chloroform was stirred at 60° C. for 5 hours. After the reaction mixture was cooled to room temperature, 10 ml of carbon tetrachrolide was added thereto, and the whole mixture was subsequently washed with water, an aqueous solution of 10% sodium bisulfite, a 2N aqueous solution of sodium hydroxide, water and saturated saline solution in that order and dried over anhydrous magnesium sulfate. After the solvent was distilled off, the residue was purified by silica gel column chromatography (eluted with benzene-ethyl acetate 15:1) to obtain 0.70 g of Compound No. 4 in Table 1.

IR spectrum (neat) cm$^{-1}$: 3560, 2926, 1577, 1071.

'H-NMR spectrum (CDCl$_3$-TMS)$^\delta$: 2.92 (3H, s), 2.90 (1H, d), 3.37 (1H, d), 4.03 (1H, d), 4.07 (1H, d), 6.73 (1H, d), 7.3 to 8.0 (9H, m).

EXAMPLE II-6

Preparation of 2-(6-chloropyridin-2-yl)-1,2-epoxy-3-[N-(4-methanesulfonylbenzenesulfonyl)-N-methylamino]propane A mixture of 1.0 g of 2-(6-chloropyridin-2-yl)-3-[N-methyl-N-(4-methylthiobenzenesulfonyl)amino]propene, 0.19 g of sodium acetate trihydrate, 2.6 g of 40% peracetic acid and 10 ml of chloroform was stirred at 60° C. for 4 hours. After the reaction mixture was cooled to room temperature, 10 ml of carbon tetrachrolide was added thereto, and the whole mixture was subsequently washed with water, an aqueous solution of 10% sodium bisulfite, a 2N aqueous solution of sodium hydroxide, water and brine in that order, and dried over anhydrous magnesium sulfate. After the solvent was distilled off, the residue was purified by silica gel column chromatography (eluted with benzene-ethyl acetate 5:1) to obtain 0.33 g of Compound No. 44 in Table 1.

IR spectrum (KBr) cm$^{-1}$: 1582, 1560, 1342, 1318, 1285, 1149.

'H-NMR spectrum (CDCl$_3$-TMS)$^\delta$: 2.84 (1H, d), 2.90 (3H, s), 3.10 (3H, s), 3.21 (1H, d), 3.79 (1H, d), 4.04 (1H, d), 7.2 to 8.2 (7H, m).

EXAMPLE II-7

Preparation of 1-bromo-3-[N-(4-chloro-3-methylbenzenesulfonyl)-N-methylamino]-2-(6-chloropyridin-2-yl)-2-hydroxypropane To a mixture of 1.0 g of 3-[N-(4-chloro-3-methylbenzenesulfonyl)-N-methylamino]-2-(6-chloropyridin-2-yl)propene, 20 ml of tetrahydrofuran and 10 ml of water, 4.79 g of N-bromosuccinimide was added, and the whole mixture was stirred at room temperature for 3 hours. An aqueous solution of 10% sodium thiosulfate was added to the reaction mixture to extract the mixture with benzene. The extract was washed with saturated saline solution and dried over anhydrous magnesium sulfate. After the solvent was distilled off, the residue was purified by silica gel column chromatography (eluted with benzene-ethyl-acetate 20:1) to obtain 0.75 g of Compound No. 56 in Table 1.

IR spectrum (neat) cm$^{-1}$: 3420, 2930, 1559, 953, 877.

'H-NMR spectrum (CCl$_4$-TMS)$^\delta$:6 2.47 (3H, s), 2.63 (3H, s), 3.38 (1H, d), 3.72 (1H, d), 3.80 (2H, s), 4.37 (1H, s), 7.2 to 7.8 (6H, m).

EXAMPLE II-8

Preparation of
1-bromo-2-(6-chloropyridin-2-yl)-2-hydroxy-3-[N-methyl-N-(5,6,7,8-tetrahydronaphthalene-2sulfonyl)amino]propane To a mixture of 1.0 g of 2-(6-chloropyridin-2-yl)-3-N-methyl-N-(5,6,7,8-tetrahydronaphthalene-2-sulfonyl)amino]propene, 10 ml of tetrahydrofuran, 10 ml of dimethylsulfoxide and 5 ml of water, 6.0 g of N-bromosuccinimide was added under stirring, and the whole mixture was stirred at room temperature for 24 hours. The reaction mixture was diluted with water to extract the mixture with benzene. The extract was washed with water and then with brine and dried over anhydrous magnesium sulfate. After the solvent was distilled off, the residue was purified by silica gel column chromatography (eluted with benzene-ethyl acetate 20:1) to obtain 0.53 g of Compound No. 89 in Table 1.

IR spectrum (neat) cm$^{-1}$: 3452, 1581, 1559, 1405, 1314.

'H-NMR spectrum (CCl$_4$-TMS)$^\delta$: 1.7 to 2.0 (4H, m), 2.62 (3H, s), 2.7 to 3.0 (4H, m), 3.35 (1H, d) 3.73 (1H, d), 3.80 (2H, s), 4.53 (1H, s), 7.1 to 7.8 (6H, m).

EXAMPLE II-9

Preparation of
1-bromo-2-(6-chloropyridin-2-yl)-2hydroxy-3-[N-methyl-(4-methanesulfinylbenzenesulfonyl)-N-methylamino]propane To a mixture of 1.3 g of 2-(6-chloropyridin-2-yl)-3-[N-methyl-N-(4-methylthiobenzenesulfonyl)amino]propene, 20 ml of tetrahydrofuran and 10 ml of water, 6.28 g of N-bromosuccinimide was added under stirring, and the whole mixture was stirred at room temperature for 2.5 hours. The reaction mixture was diluted with water to extract the mixture with benzene. The extract was washed with water and then with saturated saline solution and dried over anhydrous magnesium sulfate. After the solvent was distilled off, the residue was purified by silica gel column chromatography (eluted with chloroform-ethyl acetate 5:1) to obtain 0.82 g of Compound No. 41 in Table 1.

IR spectrum (neat) cm$^{-1}$: 3422, 1577, 1560, 1457.

'H-NMR spectrum (CDCl$_3$-TMS)$^\delta$: 2.70 (3H, s), 2.78 (3H, s), 3.48 (1H, d), 3.80 (1H, d), 3.86 (2H, s), 4.3 (1H, br.s), 7.2 to 8.0 (7H, m).

EXAMPLE II-10

Preparation of
1-[N-(4-chloro-3-methylbenzenesulfonyl)-N-methylamino]-2-(6-chloropyridin-2-yl)-2-hydroxy-3-(p-toluenesulfonyloxy)propane (a) Preparation of 1-acetoxy-3-[N-(4-chloro-3-methylbenzenesulfonyl)-N-methylamino]-2-(6-chloropyridin-2-yl)-2hydroxypropane A mixture of 7.0 g of 1-[N-(4-chloro-3-methylbenzenesulfonyl)-N-methylamino]-2-(6-chloropyridin-2-yl)-2,3-epoxypropane, 3.70 g of anhydrous sodium acetate and 60 ml of acetic acid was stirred at 100° C. for 12 hours. The reaction mixture was concentrated under a reduced pressure and 100 ml of water was added thereto. The mixture was extracted with ethyl acetate, subsequently washed with water, saturated aqueous solution of sodium bicarbonate and saturated saline solution in that order, and dried over anhydrous magnesium sulfate. After distilling off the solvent, the residue was purified by silica gel column chromatography (eluted with ethyl acetate - n-hexane 1:3 ) to obtain 5.87 g of the objective compound.

mp: 92° to 93° C.

'H-NMR spectrum (CDCL$_3$-TMS)$^\delta$: 2.00 (3H, s), 2.47 (3H, s), 2.67 (3H, s), 3.53 (2H, s), 2H, s), 4.27 (2H, s), 4.53 (1H, s), 7.2 to 7.8 (6H, m).

(b) Preparation of 1-[N-(4-chloro-3-methylbenzenesulfonyl)-N-methylamino] -2-(6-chloropyridin-2-yl)-2,3-dihydroxypropane A mixture of 1.5 g of 1-acetoxy-3-[N-(4-chloro-3-methylbenzenesulfonyl)-N-methylamino]-2-(6-chloropyridin-2-yl)-2-hydroxypropane, 1 ml of triethylamine, 1 ml of water and 2 ml of methanol was stirred at room temperature for 4 hours. The reaction mixture was left to stand overnight, and the deposited crystals were filtered out and washed with water-containing methanol to obtain 1.17 g of the objective compound.

mp: 131° to 132° C.

'H-NMR spectrum (CDCl$_3$, CD$_3$OD-TMS)$^\delta$: 2.46 (3H, s), 2.72 (3H, s), 2.8 to 3.1 (3H, br.s), 3.40 (1H, d), 3.64 (1H, d), 3.4 (1H, br), 3.84 (2H, s), 7.2 to 7.8 (6H, m).

(c) Preparation of 1-[N-(4-chloro-3-methylbenzenesulfonyl)-N-methylamino]-2-(6-chloropyridin-2-yl)-2-hydroxy-3-(p-toluenesulfonyloxy)propane A mixture of 0.50 g of 1-[N-(4-chloro-3-methylbenzenesulfonyl)-N-methylamino]-2-(6-chloropyridin-2-yl)-2,3-dihydroxypropane, 0.35 g of p-toluenesulfonyl chloride and 2.5 ml of pyridine was stirred at room temperature for 5 hours. Benzene was added to the reaction mixture, and the whole mixture was subsequently washed with water, 1N hydrochloric acid, water and brine in that order, and was then dried over anhydrous magnesium sulfate. After distilling off the solvent, the residue was purified by silica gel column chromatography (eluted with benzene - ethyl acetate 20 : (1) to obtain 0.28 g of Compound No. 60 in Table 1.

IR spectrum (KBr) cm$^{-1}$: 3500, 1335, 1159, 1097, 972.

'H-NMR spectrum (CDCl$_3$-TMS)$^\delta$: 2.47 (6H, s), 2.65 (3H, s), 3.49 (1H, d), 3.58 (1H, d), 4.29 (1 H, d), 4.33 (1H, d), 4.57 (1H, br. s), 7.2 to 7.8 (10H, m).

Example II-11

Preparation of 1-[N-(4-chloro-3-methylbenzenesulfonyl)-Nmethyamino]-2-(6-chloropyridin-2-yl)-2-hydroxy-3-methanesulfonyloxypropane A mixture of 0.80 g of 1-[N-(4-chloro-3-methylbenzenesulfonyl)-N-methylamino]-2-(6-chloropyridin-2-yl)-2,3-dihydroxypropane which had been obtained in Example II-10, 0.35 g of methanesulfonyl chloride and 4 ml of pyridine was stirred at 0° to 5° C. for 6 hours. Benzene was added to the reaction mixture, and the whole mixture was subsequently washed with water, 1N hydrochloric acid, water and brine in that order, and was then dried over anhydrous magnesium sulfate. After distilling off the solvent, the residue was purified by silica gel column chromatography (eluted with benzene - ethyl acetate 10:1) to obtain 0.60 g of Compound No. 57 in Table 1.

IR spectrum (KBr) cm$^1$: 3490, 1559, 1330, 1161, 966.

'H-NMR spectrum (CDCl$_3$-TMS)$^\delta$: 2.47 (3H, s), 2.64 (3H, s), 3.04 (3H, s), 3.40 (1H, d), 3.70 (1H, d), 4.53 (2H, s), 4.73 (1H, s), 7.2 to 7.8 (6H, m).

Example II-12

Preparation of 1,2-epoxy-3-[N-methyl-N-(p-toluenesulfonyl)amino]-2-(6-methylpyridin-2-yl)propane A mixture of 1.0 g of 1-bromo-2-hydroxy-3-[N-methyl-N-(ptoluenesulfonyl)amino]-2-(6-methylpyridin-2-yl)propane which had been obtained in Example II-7, 3 g of anhydrous potassium carbonate and 20 ml of methanol was stirred at 40° C. for 2 hours. After distilling off the solvent, water was added to the residue to extract it with ethyl acetate, and the extract was subsequently washed with water and brine, and then dried over anhydrous magnesium sulfate. After distilling off the solvent, the residue was purified by silica gel column chromatography ( eluted with benzene - ethyl acetate 15:1 ) to obtain 0.66 g of Compound No. 30 in Table 1.

IR spectrum (KBr) cm$^-$: 1592, 1459, 1341, 1167 1155.

'H-NMR spectrum (CDCl$_3$-TMS)$^\delta$: 2.42 (3H, s), 2.52 (3H, s), 2.79 (3H, s), 2.86 (1H, d), 3.18 (1 H, d), 3.78 (1H, d), 3.86 (1H, d), 7.0 to 7.8 (7H, m).

The other compounds shown in Table 1 were synthesized in the same way as in the respective Example Nos. listed in Table 1. The structures of the compounds obtained were confirmed by the IR spectra and 'H-NMR spectra. The 'H-NMR spectra data on the compounds which were obtained in the form of amorphous solids are shown in Table 2.

TABLE 1

| No. | X *1 2- | 3- | 4- | 5- | 6- | A | R | Bonding position of pyridyl group | $Y^1$ | D | E | Melting point (°C.) or refractive index/°C. | Example No. |
|---|---|---|---|---|---|---|---|---|---|---|---|---|---|
| 1 | H | H | H | H | H | — | $CH_3$ | 2- | 6-Cl | — | —O— | 103.5–105 | 5 |
| 2 | " | " | " | " | " | $CH_2$ | $CH_3$ | 2- | 6-Cl | — | —O— | 88–89 | 5 |
| 3 | " | " | " | " | " | CH=CH | $CH_3$ | 2- | 6-Cl | — | —O— | Amorphous solid | 5 |
| 4 | " | " | " | " | " | CH=CH | $CH_3$ | 2- | 6-$CF_3$ | — | —O— | Amorphous solid | 5 |
| 5 | " | " | " | " | " | $NCH_3$ | $CH_3$ | 2- | 6-Cl | — | —O— | 1.5639/25 | 4 |
| 6 | " | " | " | " | " | $NC_3H_{7-n}$ | $CH_3$ | 2- | 6-Cl | — | —O— | 1.5533/25 | 5 |
| 7 | $CF_3$ | Cl | " | " | " | — | $CH_3$ | 2- | 6-Cl | — | —O— | 1.5442/25 | 5 |
| 8 | H | $t-C_4H_9$ | " | " | " | — | $CH_3$ | 2- | 6-Cl | — | —O— | 142.5–144.5 | 5 |
| 9 | " | $CF_3$ | " | " | " | O | $CH_3$ | 2- | 6-Cl | — | —O— | 1.5380/25 | 5 |
| 10 | " | $SO_2CH_3$ | " | " | " | — | $CH_3$ | 2- | 6-Cl | — | —O— | 69–71.5 | 4 |
| 11 | " | $NO_2$ | " | " | " | — | $CH_3$ | 2- | 6-Cl | — | —O— | 124–126 | 5 |
| 12 | " | $NO_2$ | " | " | " | — | $CH_3$ | 2- | H | — | —O— | 97.5–98.5 | 12 |
| 13 | " | H | F | " | " | — | $CH_3$ | 2- | 6-Cl | — | —O— | 134.5–137.5 | 4 |
| 14 | " | " | Cl | " | " | — | $CH_3$ | 2- | 6-Cl | — | —O— | 100–101 | 4 |
| 15 | " | " | Br | " | " | — | $CH_3$ | 2- | 6-Cl | — | —O— | 95.5–96.5 | 4 |
| 16 | " | " | $CH_3$ | " | " | — | $C_2H_5$ | 2- | 6-Cl | — | —O— | 112–113 | 4 |
| 17 | " | " | $CH_3$ | " | " | — | $CH_3$ | 2- | H | — | —O— | 110.5–112.5 | 12 |
| 18 | " | " | $CH_3$ | " | " | — | $CH_3$ | 2- | H | — | —O— | 1.5552/25 | 12 |
| 19 | " | " | $CH_3$ | " | " | — | $CH_3$ | 2- | 4-Cl | — | —O— | 89–90 | 12 |
| 20 | " | " | $CH_3$ | " | " | — | $CH_3$ | 2- | 4-$CH_3$ | — | —O— | 111–113 | 12 |
| 21 | " | " | $CH_3$ | " | " | — | $CH_3$ | 2- | 6-Cl | — | —O— | 58–62 | 4 |
| 22 | " | " | $CH_3$ | " | " | O | $CH_3$ | 2- | 6-Cl | — | —O— | 1.5528/25 | 5 |
| 23 | " | " | $CH_3$ | " | " | $NC_2H_5$ | $OCH_3$ | 2- | 6-Cl | — | —O— | 165–167 | 5 |
| 24 | " | " | $CH_3$ | " | " | — | $CH_2CH=CH_2$ | 2- | 6-Cl | — | —O— | 1.5698/25 | 5 |
| 25 | " | " | $CH_3$ | " | " | — | $CH_2C\equiv CH$ | 2- | 6-Cl | — | —O— | 78–79.5 | 5 |
| 26 | " | " | $CH_3$ | " | " | — | $CH_2CF_3$ | 2- | 6-Cl | — | —O— | 1.5250/25 | 5 |
| 27 | " | " | $CH_3$ | " | " | — | CHO | 2- | 6-Cl | — | —O— | 1.5688/24 | 5 |
| 28 | " | " | $CH_3$ | " | " | — | $CH_3$ | 2- | 6-Cl | — | —O— | 121.5–122.5 | 5 |
| 29 | " | " | $CH_3$ | " | " | — | $CH_3$ | 2- | 6-Br | — | —O— | 96–98 | 12 |
| 30 | " | " | $CH_3$ | " | " | — | $CH_3$ | 2- | 6-$CH_3$ | — | —O— | 85.5–86.5 | 5 |
| 31 | " | " | $CH_3$ | " | " | — | $CH_3$ | 2- | 6-$OCH_3$ | — | —O— | 158–159 | 5 |
| 32 | " | " | $CH_3$ | " | " | — | $CH_3$ | 4- | 2,6-$Cl_2$ | — | —O— | 88–89 | 4 |
| 33 | " | " | $C_2H_3$ | " | " | — | $CH_3$ | 2- | 6-Cl | — | —O— | 90–91.5 | 5 |
| 34 | " | " | $n-C_3H_7$ | " | " | — | $CH_3$ | 2- | 6-Cl | — | —O— | 118.5–120 | 5 |
| 35 | " | " | $CH_3O$ | " | " | — | $CH_3$ | 2- | 6-Cl | — | —O— | 122–123 | 5 |
| 36 | " | " | $i-C_3H_7O$ | " | " | — | $CH_3$ | 2- | 6-Cl | — | —O— | 98–101 | 5 |
| 37 | " | " | $CF_3$ | " | " | — | $CH_3$ | 2- | 6-Cl | — | —O— | 90–92 | 5 |
| 38 | " | " | $CH_3S$ | " | " | — | $CH_3$ | 2- | 6-Cl | — | —O— | 86–88 | 1 |
| 39 | " | " | $n-C_3H_7S$ | " | " | — | $CH_3$ | 2- | 6-Cl | — | —O— | 125–127 | 12 |
| 40 | " | " | $CH_3SO$ | " | " | — | $CH_3$ | 2- | 6-Cl | OH | Br | Amorphous solid | 9 |
| 41 | " | " | $CH_3SO$ | " | " | — | $CH_3$ | 2- | 6-Cl | OH | Br | Amorphous solid | 12 |
| 42 | " | " | $n-C_3H_7SO$ | " | " | — | $CH_3$ | 2- | 6-Cl | — | —O— | Amorphous solid | 12 |
| 43 | " | " | $n-C_3H_7SO$ | " | " | — | $CH_3$ | 2- | 6-Cl | OH | Br | 105–107 | 9 |
| 44 | " | " | $CH_3SO_2$ | " | " | — | $CH_3$ | 2- | 6-Cl | — | —O— | 107–109 | 6 |

TABLE 1-continued

| No. | *1 2- | 3- | X 4- | 5- | 6- | A | R | Bonding position of pyridyl group | Y1 | D | E | Melting point (°C.) or refractive index/°C. | Example No. |
|---|---|---|---|---|---|---|---|---|---|---|---|---|---|
| 45 | " | " | n-C3H7SO2 | " | " | — | CH3 | 2- | 6-Cl | —O— | | 95-96 | 6 |
| 46 | " | " | cyc-C5H9 | " | " | — | CH3 | 2- | 6-Cl | —O— | | 108-109 | 5 |
| 47 | (CH2)4 | | H | " | " | — | CH3 | 2- | 6-Cl | —O— | | 87-88.5 | 4 |
| 48 | CH=CHCH=CH | | " | " | " | — | CH3 | 2- | 6-Cl | —O— | | 95.5-97 | 5 |
| 49 | CF3 | H | Cl | CF3 | " | — | CH3 | 2- | 6-Cl | —O— | | 113-116 | 5 |
| 50 | Cl | " | H | CH3 | " | — | CH3 | 2- | 6-Cl | —O— | | 1.5400/25 | 5 |
| 51 | CH3 | " | " | i-C3H7 | " | — | CH3 | 2- | 6-Cl | —O— | | 58-60 | 4 |
| 52 | CH3 | " | " | H | " | — | CH3 | 2- | 6-Cl | —O— | | 1.5543/25 | 5 |
| 53 | H | Cl | F | " | " | — | CH3 | 2- | 6-Cl | —O— | | 97-98 | 5 |
| 54 | " | Cl | Cl | " | " | — | CH3 | 2- | 6-Cl | —O— | | 105-107 | 5 |
| 55 | " | CH3 | Cl | " | " | — | CH3 | 2- | 6-Cl | —O— | | 92.5-94 | 4 |
| 56 | " | CH3 | Cl | " | " | — | CH3 | 2- | 6-Cl | OH | Br | Amorphous solid | 7 |
| 57 | " | CH3 | Cl | " | " | O | CH3 | 2- | 6-Cl | OH | OMs*2 | 115-116 | 11 |
| 58 | " | CH3 | Cl | " | " | — | CH3 | 2- | 6-Cl | —O— | | 68-69 | 5 |
| 59 | " | CH3 | Cl | " | " | — | CHF2 | 2- | 6-Cl | —O— | | 111-113 | 4 |
| 60 | " | CH3 | Cl | " | " | O | CH3 | 2- | 6-Cl | OH | OTs*3 | 140-142 | 10 |
| 61 | " | CH3 | Cl | " | " | — | CH3 | 2- | 6-CF3 | —O— | | 54-55 | 5 |
| 62 | " | CH3 | Cl | " | " | — | CH3 | 2- | 6-OCH3 | —O— | | 92-93.5 | 5 |
| 63 | " | CH3 | Cl | " | " | — | CH3 | 2- | 6-SO2CH3 | —O— | | 153.5-155 | 4 |
| 64 | " | CH3 | CH3 | " | " | — | CH3 | 2- | 6-Cl | —O— | | 108-111 | 5 |
| 65 | " | CH3 | CH3S | " | " | — | CH3 | 2- | 6-Cl | —O— | | 93-95 | 2 |
| 66 | " | CH3 | CH3S | " | " | — | CH3 | 2- | 6-Cl | —O— | | 86-88 | 1 |
| 67 | " | CH3 | CH3SO | " | " | — | CH3 | 2- | 6-Cl | —O— | | 125-127 | 12 |
| 68 | " | CH3 | CH3SO | " | " | — | CH3 | 2- | 6-Cl | OH | Br | Amorphous solid | 9 |
| 69 | " | CH3 | CH3SO | " | " | O | CH3 | 2- | 6-Cl | —O— | | 1.5636/25 | 12 |
| 70 | " | CH3 | CH3SO | " | " | O | CH3 | 2- | 6-Cl | OH | Br | 1.5708/25 | 9 |
| 71 | " | CH3 | CH3SO2 | " | " | O | CH3 | 2- | 6-Cl | —O— | | 121-122 | 6 |
| 72 | " | CH3 | CH3SO2 | " | " | — | CH3 | 2- | 6-Cl | —O— | | 1.5610/25 | 6 |
| 73 | " | CH3 | CH3SO2 | " | " | — | CH3 | 2- | 6-Cl | —O— | | 123-124 | 12 |
| 74 | " | CH3 | CH3SO2 | " | " | — | CH3 | 3- | 5-Br | —O— | | 165-166 | 4 |
| 75 | " | i-C3H7 | CN | " | " | — | CH3 | 4- | 2,6-Cl2 | —O— | | 120.5-122 | 4 |
| 76 | " | t-C4H9 | Cl | " | " | — | CH3 | 2- | 6-Cl | —O— | | 70-71 | 5 |
| 77 | " | CH3O | Cl | " | " | — | CH3 | 2- | 6-Cl | —O— | | 90-91 | 5 |
| 78 | " | CH3O | CH3O | " | " | — | CH3 | 2- | 6-Cl | —O— | | 144-146 | 5 |
| 79 | " | CF3 | Cl | " | " | — | CH3 | 2- | 6-Cl | —O— | | 109-111 | 5 |
| 80 | " | CCl3 | Cl | " | " | — | CH3 | 2- | 6-Cl | —O— | | 1.5829/25 | 5 |
| 81 | " | (CH2)3 | | " | " | — | CH3 | 2- | 6-Cl | —O— | | 127-129 | 5 |
| 82 | " | (CH2)2O | | " | " | — | CH3 | 2- | 6-Cl | —O— | | 106-107 | 4 |
| 83 | " | (CH2)2O | | " | " | — | CH3 | 2- | 6-OCH3 | —O— | | 115-116.5 | 5 |
| 84 | " | CH2C(CH3)2O | | " | " | — | CH3 | 2- | 6-Cl | —O— | | 168-170 | 5 |
| 85 | " | C(CH3)2CH2O | | " | " | — | CH3 | 2- | 6-Cl | —O— | | 117-119 | 5 |
| 86 | " | CH2CH(CH3)S | | " | " | — | CH3 | 2- | 6-Cl | —O— | | 119-121 | 2 |
| 87 | " | CH2CH(CH3)SO2 | | " | " | — | CH3 | 2- | 6-Cl | —O— | | 1.5481/25 | 2 |
| 88 | " | (CH2)4 | | " | " | — | CH3 | 2- | 6-Cl | —O— | | 128.5-130 | 4 |
| 89 | " | (CH2)4 | | " | " | — | CH3 | 2- | 6-Cl | OH | Br | 1.5797/25 | 8 |
| 90 | " | (CH2)4 | | " | " | — | CH3 | 2- | 6-Cl | OH | OTs | 114-116 | 10 |

TABLE 1-continued

| No. | *1 2- | 3- | X 4- | 5- | 6- | A | R | Bonding position of pyridyl group | Y¹ | D | E | Melting point (°C.) or refractive index/°C. | Example No. |
|---|---|---|---|---|---|---|---|---|---|---|---|---|---|
| 91 | 2- | | (CH₂)₄ | " | " | — | CHF₂ | 2- | 6-Cl | —O— | | 87-89 | 4 |
| 92 | " | | (CH₂)₄ | " | " | — | CHO | 2- | 6-Cl | —O— | | 1.5798/24 | 5 |
| 93 | " | | (CH₂)₄ | " | " | — | CH₃ | 2- | 6-Br | —O— | | 111-114 | 5 |
| 94 | " | | (CH₂)₄ | " | " | — | CH₃ | 2- | 6-CF₃ | —O— | | 95-98 | 5 |
| 95 | " | | (CH₂)₄ | " | " | — | CH₃ | 2- | 6-OCH₃ | —O— | | 82-82.5 | 5 |
| 96 | " | | (CH₂)₄ | " | " | — | CH₃ | 2- | 6-SO₂CH₃ | —O— | | 175-178 | 4 |
| 97 | " | | (CH₂)₄ | " | " | — | CH₃ | 4- | 2,6-Cl₂ | —O— | | 114-115 | 4 |
| 98 | " | | (CH₂)₃S | " | " | — | CH₃ | 2- | 6-Cl | —O— | | 121-122 | 2 |
| 99 | " | | (CH₂)₃SO | " | " | — | CH₃ | 2- | 6-Cl | —O— | | Amorphous solid | 2 |
| 100 | " | | (CH₂)₃SO₂ | " | " | — | CH₃ | 2- | 6-Cl | —O— | | 172-174 | 2 |
| 101 | " | | O(CH₂)₃O | " | " | — | CH₃ | 2- | 6-Cl | —O— | | 163-166 | 5 |
| 102 | " | | CH=CHCH=CH | " | " | — | CH₃ | 2- | 6-Cl | —O— | | 126-130 | 5 |
| 103 | " | | CH=CHCH=CH | " | " | O | CH₃ | 2- | 6-Cl | —O— | | 1.5990/25 | 5 |
| 104 | " | Cl | H | Cl | " | — | CH₃ | 2- | 6-Cl | —O— | | 134.5-135.5 | 5 |
| 105 | CH₃ | H | CH₃ | H | CH₃ | — | CH₃ | 2- | 6-Cl | —O— | | 82-83 | 5 |

*¹2-, 3-, 4-, 5- and 6- represent the substitution position of X in a benzene ring.
*²OMs represents a methanesulfonyloxy group.
*³OTs represents a p-toluenesulfonyloxy group.

TABLE 2

| Compound No. | Chemical shift of $^1$H-NMR Spectrum (solvent-TMS)$^\delta$ |
|---|---|
| 3 | (CDCl$_3$) 2.83($^1$H,d.), 2.90(3H,s.), 3.27($^1$H,d.), 3.93($^1$H,d.), 4.03($^1$H,d.), 6.73($^1$H,d.), 7.2–7.8(9H,m.) |
| 4 | (CDCl$_3$) 2.90($^1$H,d.), 2.92(3H,s.), 3.37($^1$H,d.), 4.02($^1$H,d.), 4.07($^1$H,d.), 6.73($^1$H,d.), 7.3–8.0(9H,m.) |
| 42 | (CDCl$_3$) 1.08(3H,t.), 1.5–2.1(2H,m.), 2.82(2H,t.), 2.85($^1$H,d.), 2.89(3H,s.), 3.22($^1$H,d.), 3.82($^1$H,d.), 4.00($^1$H,d.), 7.2–8.1(7H,m.) |
| 68 | (CDCl$_3$) 2.45(3H,s.), 2.70(3H,s.), 2.73(3H,s.), 3.49($^1$H,d.), 3.77($^1$H,d.), 3.87(2H,s.), 4.0–4.3($^1$H,br.s.), 7.3–8.3(6H,m.) |
| 99 | (CDCl$_3$) 2.15–2.58(2H,m.), 2.72–2.96(3H,m.), 2.86(3H,m.), 3.05–3.28(3H,m.), 3.71($^1$H,d.), 4.02($^1$H,d.), 7.27($^1$H,d.), 7.33($^1$H,d.), 7.55–7.77(3H,m.), 7.90($^1$H,dd.) |

Examples of formulation processes from a compound according to the present invention will be shown in the following. "Part" and "%" hereinunder represent "part by weight" and "% by weight", respectively.

Formulation Example 1: Wettable Powder 40 parts of a compound of the present invention (Compound No. 7 in Table 1), 20 parts of Carplex #80 (trade mark, produced by Shionogi & Co., Ltd.), 35 parts of N,N-kaolin clay (trade mark, produced by Tsuchiya Kaolin Co., Ltd.) and 5 parts of a higher alkali sulfate surfactant Sorpol 8070 (trade mark, produced by Toho Kagaku Co., Ltd.) were uniformly mixed and pulverized to obtain a wettable powder containing 40% of a active ingredient.

Formulation 2: Granules 2 parts of a compound of the present invention (Compound No. 3 in Table 1), 42 parts of clay (produced by Nippon Talc Co., Ltd.), 55 parts of bentonite (produced by Hojun Yoko Co., Ltd.) and 1 part of a succinate surfactant Aerol CT-1 (produced by Toho Kagaku Co., Ltd.) were mixed and pulverized. The resultant mixture was kneaded with 20 parts of water and extruded from the nozzles of 0.6 m in diameter of an extrusion pelletizer. The extruded pieces were dried at 60° C. for 2 hours and were then cut into a length of 1 to 2 mm, thereby obtaining granules containing 2% of a active ingredient.

Formulation Example 3: Emulsifiable concentrate

An emulsion containing 30% of an active ingredient was prepared by dissolving 30 parts of a compound of the present invention (Compound No. 7 in Table 1) into a mixed solvent of 30 parts of xylene and 25 parts of dimethylformamide, and adding 15 parts of a polyoxyethylene surfactant Sorpol 3005X (trade mark, produced by Toho Kagaku Co., Ltd.)

Formulation Example 4: Suspension concentrate 30 parts of a compound of the present invention (Compound No. 1 in Table 1) was adequately mixed with and dispersed in a mixture of 8 parts of ethylene glycol, 5 parts of Sorpol AC3032 (trade mark, Toho Kagak Co.,Ltd.), 0.1 part of xanthan gum and 56.9% of water. The thus-obtained mixture in the form of slurry was wet-milled by a Dyno-mill (produced by Symmal Enterprise Co., Ltd.) to obtain a stable suspension concentrate containing 30% of an active ingredient.

Experiment 1

Preemergence and early postemergence flooded paddy field test on weeds and phytotoxicity test on rice plant A plastic pot having an area of 1/5000 are was charged with the alluvial clay loam of a rice field, and the soil was fertilized and plowed while adding an appropriate amount of water thereto. On the thus-prepared soil, the seeds of weeds Echinochloa crus-galli, Cyperus Difformis and Scripus uncoides were sown. The seeds were mixed well with the soil in the layer within 1 cm of the surface and 2.1th-stage seedlings of rice plants (species: Akinishiki, height: 9.5 cm, quality: good) were planted at a depth of about 1 cm (2 plants per pot). Thereafter, the water was maintained at a depth of 3.5 cm, and the tubers of Cyperus serotinus were planted on the surface of the soil (3 tubers per pot).

On the next day and the seventh day after the transplantation, granules which contained the respective compounds shown in Table 3 and which had been obtained in the same way as in Formulation Example 2 were dropped to the flooded surfaces. For comparison, granules which contained 4-n-propyl-N-(2,3-epoxy-2-phenylpropyl)-N-α-methylbenzylbenzenesulfonamide (hereinuder referred to as "Comparative Compound A") and N-(2,3-epoxypropylene)-N-α-methylbenzylbenzenesulfonamide (hereinuder referred to as "Comparative Compound B"), respectively, as the active ingredient, and which had been obtained in the same way as in Formulation Example 2 were dropped to the flooded surfaces. The amounts of granules used were respectively so that the doses of active ingredients contained were 10 g and 5 g, respectively, per are. The leaf stage of the weeds at the time of treating were as follows.

Plot treated on the next day after the transplantation: No weeds were germinated.

Plot treated on the seventh day after the transplantation:

Echinochloa crus-galli: 1 to 1.5 l

Cyperus difformis, Scripus juncoides: 1 l

Cyperus serotinus: 3 to 5cm

After the treatment of the soil with the granules, a leaching loss of water was given at the rate of 3 cm/day for 2 days. On the 28th day after the herbicidal treatment, the herbicidal effect and phytotoxicity by the herbicide were observed, and the results are shown in Table 3.

The following formula was calculated and the evaluation of the herbicidal effect was represented by the herbicidal index based on the results of calculation in accordance with the following criteria:

$$\left(1 - \frac{\text{weight of the whole weeds on the surface of the soil in the treated plot}}{\text{weight of the whole weeds on the surface of the soil in the untreated plot}}\right) \times 100 = Y(\%)$$

| Herbicidal index | Y (%) |
|---|---|
| 0 | 0 to 4 |
| 1 | 5 to 29 |

| Herbicidal index | Y (%) |
|---|---|
| 2 | 30 to 49 |
| 3 | 50 to 69 |
| 4 | 70 to 89 |
| 5 | 90 to 100 |

The phytotoxicity by the herbicide to the paddy-rice plants was evaluated on the basis of the following criteria.

| phytotoxicity index | Degree of phytotoxicity |
|---|---|
| 0 | No damaged (0-4%) |
| 1 | Slight damage (5-9%) |
| 2 | Small damage (10-19%) |
| 3 | Medium damage (20-39%) |
| 4 | Great damage (40-59%) |
| 5 | Serious damage to death (60-100%) |

TABLE 3

| | | Next day after transplantation | | | | | 7th day after transplantation | | | | |
|---|---|---|---|---|---|---|---|---|---|---|---|
| | | Damage to young rice plant | Herbicidal effect | | | | Damage to young rice plant | Herbicidal effect | | | |
| Compound No. | Dose of active ingredient (g/a) | | Echinochloa crusgalli | Cyperus difformis | Scripus juncoides | Cyperus serotinus | | Echinochloa crusgalli | Cyperus difformis | Scripus juncoides | Cyperus serotinus |
| 1 | 10 | 3 | 5 | 5 | 5 | 5 | 3 | 5 | 5 | 5 | 5 |
| | 5 | 2 | 5 | 5 | 5 | 5 | 1 | 5 | 5 | 5 | 5 |
| 2 | 10 | 0 | 4 | 5 | 4 | 4 | 0 | 3 | 4 | 4 | 4 |
| | 5 | 0 | 4 | 5 | 3 | 3 | 0 | 3 | 4 | 2 | 3 |
| 3 | 10 | 1 | 5 | 5 | 5 | 5 | 0 | 5 | 5 | 5 | 5 |
| | 5 | 0 | 5 | 5 | 5 | 5 | 0 | 5 | 5 | 5 | 5 |
| 4 | 10 | 3 | 5 | 5 | 5 | 5 | 3 | 5 | 5 | 5 | 5 |
| | 5 | 3 | 5 | 5 | 5 | 5 | 2 | 5 | 5 | 5 | 5 |
| 5 | 10 | 2 | 5 | 5 | 5 | 5 | 1 | 5 | 5 | 5 | 4 |
| | 5 | 1 | 5 | 5 | 5 | 4 | 0 | 4 | 5 | 4 | 2 |
| 6 | 10 | 0 | 5 | 5 | 5 | 5 | 0 | 5 | 5 | 5 | 5 |
| | 5 | 0 | 4 | 4 | 3 | 3 | 0 | 3 | 3 | 2 | 3 |
| 7 | 10 | 4 | 5 | 5 | 5 | 5 | 3 | 5 | 5 | 5 | 5 |
| | 5 | 3 | 5 | 5 | 5 | 5 | 2 | 5 | 5 | 5 | 5 |
| 8 | 10 | 3 | 5 | 5 | 5 | 5 | 2 | 5 | 5 | 5 | 5 |
| | 5 | 1 | 5 | 5 | 5 | 5 | 0 | 5 | 5 | 5 | 5 |
| 9 | 10 | 0 | 5 | 5 | 3 | 4 | 0 | 5 | 5 | 3 | 3 |
| | 5 | 0 | 5 | 5 | 2 | 2 | 0 | 4 | 4 | 2 | 2 |
| 10 | 10 | 3 | 5 | 5 | 5 | 5 | 3 | 5 | 5 | 5 | 5 |
| | 5 | 2 | 5 | 5 | 5 | 5 | 1 | 5 | 5 | 5 | 5 |
| 11 | 10 | 3 | 5 | 5 | 5 | 5 | 2 | 5 | 5 | 5 | 5 |
| | 5 | 1 | 5 | 5 | 5 | 5 | 0 | 5 | 5 | 4 | 4 |
| 12 | 10 | 1 | 4 | 5 | 4 | 4 | 0 | 5 | 5 | 3 | 3 |
| | 5 | 0 | 4 | 5 | 3 | 3 | 0 | 4 | 4 | 2 | 2 |
| 13 | 10 | 3 | 5 | 5 | 5 | 5 | 2 | 5 | 5 | 5 | 5 |
| | 5 | 1 | 5 | 5 | 4 | 5 | 0 | 5 | 5 | 4 | 5 |
| 14 | 10 | 3 | 5 | 5 | 5 | 5 | 3 | 5 | 5 | 5 | 5 |
| | 5 | 2 | 5 | 5 | 5 | 5 | 2 | 5 | 5 | 5 | 5 |
| 15 | 10 | 3 | 5 | 5 | 5 | 5 | 2 | 5 | 5 | 5 | 5 |
| | 5 | 1 | 5 | 5 | 5 | 5 | 1 | 5 | 5 | 5 | 5 |
| 16 | 10 | 3 | 5 | 5 | 5 | 5 | 2 | 5 | 5 | 5 | 5 |
| | 5 | 1 | 5 | 5 | 5 | 5 | 1 | 5 | 5 | 5 | 5 |
| 17 | 10 | 2 | 5 | 5 | 5 | 5 | 1 | 5 | 5 | 5 | 5 |
| | 5 | 1 | 5 | 5 | 5 | 5 | 0 | 5 | 5 | 5 | 5 |
| 18 | 10 | 0 | 5 | 5 | 4 | 5 | 0 | 5 | 5 | 4 | 5 |
| | 5 | 0 | 5 | 5 | 4 | 5 | 0 | 4 | 5 | 4 | 4 |
| 19 | 10 | 1 | 5 | 5 | 5 | 5 | 0 | 5 | 5 | 5 | 5 |
| | 5 | 0 | 5 | 5 | 4 | 5 | 0 | 5 | 5 | 4 | 5 |
| 20 | 10 | 0 | 5 | 5 | 5 | 5 | 0 | 5 | 4 | 5 | 4 |
| | 5 | 0 | 5 | 4 | 4 | 4 | 0 | 5 | 4 | 5 | 3 |
| 21 | 10 | 2 | 5 | 5 | 5 | 5 | 1 | 5 | 5 | 5 | 5 |
| | 5 | 1 | 5 | 5 | 5 | 5 | 0 | 5 | 5 | 5 | 5 |
| 22 | 10 | 2 | 5 | 5 | 5 | 5 | 1 | 5 | 5 | 5 | 4 |
| | 5 | 1 | 5 | 5 | 4 | 4 | 0 | 5 | 5 | 3 | 2 |
| 23 | 10 | 0 | 5 | 5 | 5 | 5 | 0 | 5 | 5 | 5 | 5 |
| | 5 | 0 | 5 | 5 | 4 | 4 | 0 | 5 | 5 | 4 | 4 |
| 24 | 10 | 0 | 5 | 5 | 4 | 5 | 0 | 4 | 5 | 4 | 5 |
| | 5 | 0 | 5 | 5 | 3 | 4 | 0 | 3 | 4 | 3 | 4 |
| 25 | 10 | 2 | 5 | 5 | 5 | 5 | 1 | 5 | 5 | 4 | 5 |
| | 5 | 1 | 5 | 5 | 4 | 5 | 0 | 4 | 5 | 3 | 5 |
| 26 | 10 | 3 | 5 | 5 | 5 | 5 | 2 | 4 | 5 | 4 | 5 |
| | 5 | 1 | 5 | 5 | 4 | 5 | 0 | 3 | 5 | 3 | 5 |
| 27 | 10 | 0 | 5 | 5 | 5 | 5 | 0 | 3 | 5 | 2 | 3 |
| | 5 | 0 | 5 | 5 | 4 | 5 | 0 | 2 | 4 | 2 | 2 |
| 28 | 10 | 0 | 5 | 5 | 5 | 5 | 0 | 4 | 5 | 4 | 4 |
| | 5 | 0 | 4 | 5 | 4 | 5 | 0 | 3 | 4 | 2 | 2 |
| 29 | 10 | 3 | 5 | 5 | 5 | 5 | 2 | 5 | 5 | 5 | 5 |
| | 5 | 0 | 5 | 5 | 5 | 5 | 0 | 5 | 5 | 5 | 4 |
| 30 | 10 | 1 | 5 | 5 | 5 | 5 | 0 | 5 | 5 | 5 | 5 |
| | 5 | 0 | 5 | 5 | 4 | 5 | 0 | 5 | 5 | 5 | 5 |
| 31 | 10 | 3 | 5 | 5 | 5 | 5 | 3 | 5 | 5 | 5 | 5 |
| | 5 | 2 | 5 | 5 | 5 | 5 | 1 | 5 | 5 | 5 | 5 |

TABLE 3-continued

|  |  | Next day after transplantation | | | | | 7th day after transplantation | | | | |
|---|---|---|---|---|---|---|---|---|---|---|---|
|  |  | Herbicidal effect | | | | | Herbicidal effect | | | | |
| Compound No. | Dose of active ingredient (g/a) | Damage to young rice plant | Echino-chloa crus-galli | Cyperus difformis | Scripus juncoides | Cyperus serotinus | Damage to young rice plant | Echino-chloa crus-galli | Cyperus difformis | Scripus juncoides | Cyperus serotinus |
| 32 | 10 | 0 | 5 | 5 | 5 | 5 | 0 | 5 | 5 | 3 | 3 |
|  | 5 | 0 | 5 | 5 | 4 | 4 | 0 | 5 | 4 | 2 | 2 |
| 33 | 10 | 3 | 5 | 5 | 5 | 5 | 2 | 5 | 5 | 5 | 5 |
|  | 5 | 2 | 5 | 5 | 5 | 5 | 1 | 5 | 5 | 5 | 5 |
| 34 | 10 | 2 | 5 | 5 | 5 | 5 | 1 | 5 | 5 | 5 | 5 |
|  | 5 | 0 | 5 | 5 | 5 | 5 | 0 | 5 | 5 | 5 | 5 |
| 35 | 10 | 3 | 5 | 5 | 5 | 5 | 2 | 5 | 5 | 5 | 5 |
|  | 5 | 2 | 5 | 5 | 5 | 5 | 1 | 5 | 5 | 5 | 5 |
| 36 | 10 | 0 | 5 | 5 | 5 | 5 | 0 | 5 | 5 | 4 | 5 |
|  | 5 | 0 | 5 | 5 | 4 | 5 | 0 | 5 | 5 | 4 | 5 |
| 37 | 10 | 1 | 5 | 5 | 5 | 5 | 0 | 5 | 5 | 5 | 5 |
|  | 5 | 0 | 5 | 5 | 5 | 5 | 0 | 5 | 5 | 5 | 5 |
| 38 | 10 | 0 | 5 | 5 | 5 | 5 | 0 | 5 | 5 | 5 | 5 |
|  | 5 | 0 | 5 | 5 | 5 | 5 | 0 | 5 | 5 | 4 | 5 |
| 39 | 10 | 0 | 5 | 5 | 5 | 5 | 0 | 4 | 5 | 4 | 4 |
|  | 5 | 0 | 5 | 5 | 4 | 5 | 0 | 3 | 4 | 3 | 2 |
| 40 | 10 | 3 | 5 | 5 | 5 | 5 | 3 | 5 | 5 | 5 | 5 |
|  | 5 | 3 | 5 | 5 | 5 | 5 | 2 | 5 | 5 | 5 | 5 |
| 41 | 10 | 2 | 5 | 5 | 5 | 5 | 1 | 5 | 5 | 5 | 5 |
|  | 5 | 1 | 5 | 5 | 4 | 5 | 0 | 5 | 5 | 4 | 5 |
| 42 | 10 | 3 | 5 | 5 | 5 | 5 | 3 | 5 | 5 | 5 | 5 |
|  | 5 | 2 | 5 | 5 | 5 | 5 | 1 | 5 | 5 | 5 | 5 |
| 43 | 10 | 3 | 5 | 5 | 5 | 5 | 3 | 5 | 5 | 5 | 5 |
|  | 5 | 3 | 5 | 5 | 5 | 5 | 2 | 5 | 5 | 5 | 5 |
| 44 | 10 | 3 | 5 | 5 | 5 | 5 | 2 | 5 | 5 | 5 | 5 |
|  | 5 | 2 | 5 | 5 | 4 | 5 | 1 | 5 | 5 | 4 | 5 |
| 45 | 10 | 3 | 5 | 5 | 5 | 5 | 3 | 5 | 5 | 5 | 5 |
|  | 5 | 3 | 5 | 5 | 5 | 5 | 2 | 5 | 5 | 5 | 5 |
| 46 | 10 | 0 | 5 | 5 | 4 | 5 | 0 | 4 | 5 | 5 | 5 |
|  | 5 | 0 | 5 | 5 | 4 | 5 | 0 | 3 | 5 | 3 | 5 |
| 47 | 10 | 2 | 5 | 5 | 5 | 5 | 1 | 5 | 5 | 5 | 5 |
|  | 5 | 1 | 5 | 5 | 5 | 5 | 0 | 5 | 5 | 5 | 5 |
| 48 | 10 | 2 | 5 | 5 | 5 | 5 | 2 | 5 | 5 | 5 | 5 |
|  | 5 | 1 | 5 | 5 | 5 | 5 | 0 | 5 | 5 | 5 | 5 |
| 49 | 10 | 1 | 5 | 5 | 5 | 5 | 1 | 5 | 5 | 5 | 5 |
|  | 5 | 0 | 5 | 5 | 5 | 5 | 0 | 5 | 5 | 5 | 5 |
| 50 | 10 | 2 | 5 | 5 | 5 | 5 | 1 | 5 | 5 | 5 | 5 |
|  | 5 | 1 | 5 | 5 | 5 | 5 | 1 | 5 | 5 | 5 | 5 |
| 51 | 10 | 3 | 5 | 5 | 5 | 5 | 3 | 5 | 5 | 5 | 5 |
|  | 5 | 1 | 5 | 5 | 5 | 5 | 1 | 5 | 5 | 5 | 5 |
| 52 | 10 | 2 | 5 | 5 | 5 | 5 | 2 | 5 | 5 | 5 | 5 |
|  | 5 | 0 | 5 | 5 | 4 | 5 | 0 | 5 | 5 | 4 | 4 |
| 53 | 10 | 3 | 5 | 5 | 5 | 5 | 3 | 5 | 5 | 5 | 5 |
|  | 5 | 2 | 5 | 5 | 5 | 5 | 1 | 5 | 5 | 5 | 5 |
| 54 | 10 | 0 | 5 | 5 | 5 | 5 | 0 | 5 | 5 | 4 | 5 |
|  | 5 | 0 | 5 | 5 | 4 | 5 | 0 | 5 | 5 | 3 | 5 |
| 55 | 10 | 1 | 5 | 5 | 5 | 5 | 0 | 5 | 5 | 5 | 5 |
|  | 5 | 0 | 5 | 5 | 5 | 5 | 0 | 5 | 5 | 5 | 5 |
| 56 | 10 | 1 | 5 | 5 | 5 | 5 | 0 | 5 | 5 | 4 | 5 |
|  | 5 | 0 | 5 | 5 | 4 | 5 | 0 | 5 | 5 | 3 | 5 |
| 57 | 10 | 1 | 5 | 5 | 5 | 5 | 0 | 5 | 5 | 4 | 5 |
|  | 5 | 0 | 5 | 5 | 4 | 5 | 0 | 5 | 5 | 3 | 5 |
| 58 | 10 | 0 | 5 | 5 | 3 | 4 | 0 | 5 | 5 | 4 | 4 |
|  | 5 | 0 | 5 | 5 | 2 | 3 | 0 | 5 | 5 | 2 | 4 |
| 59 | 10 | 0 | 5 | 5 | 4 | 5 | 0 | 5 | 5 | 4 | 5 |
|  | 5 | 0 | 5 | 5 | 4 | 5 | 0 | 5 | 5 | 4 | 5 |
| 60 | 10 | 0 | 4 | 5 | 4 | 4 | 0 | 3 | 4 | 2 | 2 |
|  | 5 | 0 | 4 | 4 | 3 | 3 | 0 | 2 | 4 | 2 | 1 |
| 61 | 10 | 1 | 5 | 5 | 5 | 5 | 0 | 5 | 5 | 5 | 5 |
|  | 5 | 0 | 5 | 5 | 5 | 5 | 0 | 5 | 5 | 5 | 5 |
| 62 | 10 | 1 | 5 | 5 | 5 | 5 | 0 | 5 | 5 | 5 | 5 |
|  | 5 | 0 | 5 | 5 | 5 | 5 | 0 | 5 | 5 | 5 | 4 |
| 64 | 10 | 3 | 5 | 5 | 5 | 5 | 2 | 5 | 5 | 5 | 5 |
|  | 5 | 1 | 5 | 5 | 5 | 5 | 0 | 5 | 5 | 5 | 5 |
| 65 | 10 | 0 | 5 | 5 | 5 | 5 | 0 | 5 | 5 | 4 | 5 |
|  | 5 | 0 | 5 | 5 | 4 | 5 | 0 | 5 | 5 | 4 | 3 |
| 66 | 10 | 0 | 5 | 5 | 5 | 5 | 0 | 5 | 5 | 4 | 5 |
|  | 5 | 0 | 5 | 5 | 4 | 5 | 0 | 5 | 5 | 3 | 4 |
| 67 | 10 | 0 | 5 | 5 | 5 | 5 | 0 | 5 | 5 | 4 | 5 |
|  | 5 | 0 | 5 | 5 | 4 | 5 | 0 | 5 | 5 | 3 | 5 |
| 68 | 10 | 0 | 5 | 5 | 5 | 5 | 0 | 5 | 5 | 4 | 5 |
|  | 5 | 0 | 5 | 5 | 4 | 5 | 0 | 5 | 5 | 3 | 5 |
| 69 | 10 | 0 | 5 | 5 | 5 | 5 | 0 | 5 | 5 | 4 | 5 |
|  | 5 | 0 | 5 | 5 | 4 | 5 | 0 | 5 | 5 | 3 | 5 |
| 70 | 10 | 0 | 5 | 5 | 5 | 5 | 0 | 5 | 5 | 4 | 5 |

TABLE 3-continued

| | | Next day after transplantation | | | | 7th day after transplantation | | | | |
| | | Herbicidal effect | | | | Herbicidal effect | | | | |
| Compound No. | Dose of active ingredient (g/a) | Damage to young rice plant | Echinochloa crusgalli | Cyperus difformis | Scripus juncoides | Cyperus serotinus | Damage to young rice plant | Echinochloa crusgalli | Cyperus difformis | Scripus juncoides | Cyperus serotinus |
|---|---|---|---|---|---|---|---|---|---|---|---|
| 71 | 5 | 0 | 5 | 5 | 4 | 5 | 0 | 5 | 5 | 3 | 5 |
| | 10 | 1 | 5 | 5 | 5 | 5 | 0 | 5 | 5 | 5 | 5 |
| 72 | 5 | 1 | 5 | 5 | 4 | 5 | 0 | 5 | 5 | 4 | 5 |
| | 10 | 0 | 5 | 5 | 5 | 5 | 0 | 5 | 5 | 4 | 5 |
| 73 | 5 | 0 | 5 | 5 | 4 | 5 | 0 | 5 | 5 | 4 | 5 |
| | 10 | 0 | 5 | 5 | 5 | 5 | 0 | 5 | 5 | 3 | 3 |
| 74 | 5 | 0 | 5 | 5 | 4 | 4 | 0 | 5 | 4 | 2 | 2 |
| | 10 | 0 | 5 | 5 | 5 | 5 | 0 | 4 | 5 | 5 | 4 |
| 75 | 5 | 0 | 5 | 5 | 4 | 4 | 0 | 4 | 4 | 3 | 3 |
| | 10 | 3 | 5 | 5 | 5 | 5 | 3 | 5 | 5 | 5 | 5 |
| 76 | 5 | 2 | 5 | 5 | 5 | 5 | 2 | 5 | 5 | 5 | 5 |
| | 10 | 0 | 5 | 5 | 4 | 5 | 0 | 5 | 5 | 4 | 5 |
| 77 | 5 | 0 | 5 | 5 | 3 | 4 | 0 | 5 | 5 | 3 | 4 |
| | 10 | 0 | 5 | 5 | 3 | 5 | 0 | 5 | 5 | 3 | 5 |
| 78 | 5 | 0 | 5 | 5 | 2 | 4 | 0 | 5 | 5 | 2 | 4 |
| | 10 | 3 | 5 | 5 | 5 | 5 | 2 | 5 | 5 | 5 | 5 |
| 79 | 5 | 1 | 5 | 5 | 5 | 5 | 0 | 5 | 5 | 5 | 5 |
| | 10 | 2 | 5 | 5 | 5 | 5 | 1 | 5 | 5 | 4 | 5 |
| 80 | 5 | 0 | 5 | 5 | 4 | 5 | 0 | 5 | 5 | 4 | 5 |
| | 10 | 0 | 5 | 5 | 4 | 5 | 0 | 5 | 5 | 4 | 5 |
| 81 | 5 | 0 | 4 | 5 | 3 | 4 | 0 | 4 | 4 | 3 | 4 |
| | 10 | 0 | 5 | 5 | 5 | 5 | 0 | 5 | 5 | 5 | 5 |
| 82 | 5 | 0 | 5 | 5 | 5 | 5 | 0 | 5 | 5 | 5 | 5 |
| | 10 | 1 | 5 | 5 | 5 | 5 | 0 | 5 | 5 | 5 | 5 |
| 83 | 5 | 0 | 5 | 5 | 5 | 5 | 0 | 5 | 5 | 5 | 5 |
| | 10 | 3 | 5 | 5 | 5 | 5 | 3 | 5 | 5 | 5 | 5 |
| 84 | 5 | 1 | 5 | 5 | 5 | 5 | 0 | 5 | 5 | 5 | 4 |
| | 10 | 1 | 5 | 5 | 5 | 5 | 0 | 5 | 5 | 5 | 5 |
| 85 | 5 | 0 | 4 | 5 | 4 | 4 | 0 | 4 | 4 | 3 | 3 |
| | 10 | 0 | 5 | 5 | 5 | 5 | 0 | 5 | 5 | 5 | 5 |
| 86 | 5 | 0 | 5 | 5 | 4 | 5 | 0 | 5 | 5 | 3 | 5 |
| | 10 | 1 | 5 | 5 | 5 | 5 | 0 | 5 | 5 | 5 | 5 |
| 87 | 5 | 0 | 5 | 5 | 4 | 4 | 0 | 5 | 5 | 4 | 5 |
| | 10 | 3 | 5 | 5 | 5 | 5 | 3 | 5 | 5 | 5 | 5 |
| 88 | 5 | 3 | 5 | 5 | 5 | 5 | 2 | 5 | 5 | 4 | 5 |
| | 10 | 0 | 5 | 5 | 5 | 5 | 0 | 5 | 5 | 5 | 5 |
| 89 | 5 | 0 | 5 | 5 | 4 | 5 | 0 | 5 | 5 | 5 | 5 |
| | 10 | 0 | 5 | 5 | 5 | 5 | 0 | 5 | 5 | 5 | 5 |
| 90 | 5 | 0 | 5 | 5 | 4 | 5 | 0 | 5 | 5 | 4 | 5 |
| | 10 | 0 | 5 | 5 | 5 | 5 | 0 | 5 | 4 | 3 | 3 |
| 91 | 5 | 0 | 5 | 5 | 4 | 4 | 0 | 5 | 4 | 2 | 2 |
| | 10 | 0 | 5 | 5 | 5 | 5 | 0 | 5 | 5 | 5 | 5 |
| 92 | 5 | 0 | 5 | 5 | 5 | 5 | 0 | 5 | 5 | 4 | 5 |
| | 10 | 0 | 4 | 5 | 4 | 4 | 0 | 3 | 4 | 4 | 4 |
| 93 | 5 | 0 | 4 | 5 | 3 | 3 | 0 | 3 | 4 | 2 | 3 |
| | 10 | 0 | 5 | 5 | 4 | 4 | 0 | 5 | 5 | 4 | 4 |
| 94 | 5 | 0 | 4 | 4 | 3 | 3 | 0 | 4 | 4 | 2 | 3 |
| | 10 | 0 | 5 | 5 | 5 | 5 | 0 | 5 | 5 | 4 | 5 |
| 95 | 5 | 0 | 5 | 5 | 4 | 5 | 0 | 5 | 5 | 4 | 5 |
| | 10 | 1 | 5 | 5 | 5 | 5 | 0 | 5 | 5 | 5 | 5 |
| 97 | 5 | 0 | 5 | 5 | 4 | 5 | 0 | 5 | 5 | 5 | 5 |
| | 10 | 0 | 5 | 5 | 5 | 5 | 0 | 4 | 5 | 3 | 3 |
| 98 | 5 | 0 | 5 | 5 | 4 | 4 | 0 | 3 | 4 | 2 | 2 |
| | 10 | 0 | 5 | 5 | 5 | 5 | 0 | 5 | 5 | 4 | 5 |
| 99 | 5 | 0 | 5 | 5 | 5 | 5 | 0 | 5 | 5 | 4 | 5 |
| | 10 | 3 | 5 | 5 | 5 | 5 | 2 | 5 | 5 | 5 | 5 |
| 100 | 5 | 1 | 5 | 5 | 5 | 5 | 0 | 3 | 5 | 4 | 4 |
| | 10 | 3 | 5 | 5 | 5 | 5 | 3 | 5 | 5 | 5 | 5 |
| 101 | 5 | 3 | 5 | 5 | 5 | 5 | 2 | 5 | 5 | 5 | 5 |
| | 10 | 1 | 5 | 5 | 5 | 5 | 0 | 5 | 5 | 5 | 5 |
| 102 | 5 | 0 | 5 | 5 | 5 | 5 | 0 | 5 | 5 | 5 | 5 |
| | 10 | 1 | 5 | 5 | 5 | 5 | 0 | 5 | 5 | 5 | 5 |
| 103 | 5 | 0 | 5 | 5 | 4 | 5 | 0 | 5 | 5 | 5 | 5 |
| | 10 | 0 | 5 | 5 | 3 | 4 | 0 | 5 | 5 | 3 | 4 |
| 104 | 5 | 0 | 4 | 4 | 2 | 3 | 0 | 3 | 3 | 2 | 4 |
| | 10 | 1 | 5 | 5 | 5 | 5 | 0 | 5 | 5 | 5 | 5 |
| 105 | 5 | 0 | 5 | 5 | 5 | 5 | 0 | 5 | 5 | 4 | 5 |
| | 10 | 1 | 5 | 5 | 5 | 5 | 1 | 5 | 5 | 5 | 5 |
| | 5 | 0 | 5 | 5 | 5 | 5 | 0 | 5 | 5 | 5 | 5 |
| Comparative Compound A*1 | 10 | 0 | 0 | 3 | 0 | 0 | 0 | 0 | 1 | 0 | 0 |
| | 5 | 0 | 0 | 1 | 0 | 0 | 0 | 0 | 1 | 0 | 0 |
| Comparative Compound B*2 | 10 | 1 | 5 | 5 | 5 | 0 | 0 | 2 | 5 | 1 | 0 |
| | 5 | 0 | 5 | 5 | 4 | 0 | 0 | 0 | 2 | 0 | 0 |

TABLE 3-continued

| | | Next day after transplantation | | | | | 7th day after transplantation | | | | |
|---|---|---|---|---|---|---|---|---|---|---|---|
| | | Herbicidal effect | | | | | Herbicidal effect | | | | |
| Compound No. | Dose of active ingredient (g/a) | Damage to young rice plant | Echinochloa crusgalli | Cyperus difformis | Scripus juncoides | Cyperus serotinus | Damage to young rice plant | Echinochloa crusgalli | Cyperus difformis | Scripus juncoides | Cyperus serotinus |
| Untreated plot | — | 0 | 0 | 0 | 0 | 0 | 0 | 0 | 0 | 0 | 0 |

*1 Comparative Compound A: Compound described in Japanese Patent Application Laid-Open (KOKAI) No. 58-131977 (1983)

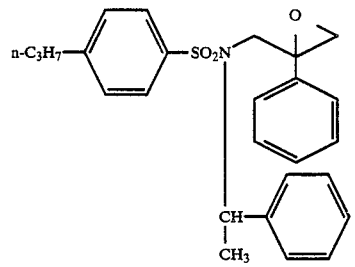

*2 Comparative Compound B: Compound described in Japanese Patent Application Laid-Open (KOKAI) No. 58-131977 (1983)

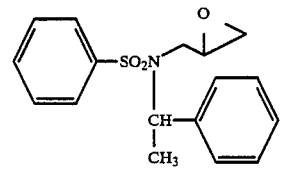

Experiment 2

Postemergence flooded paddy field test on Echinochloa crus-galli by leaf stages

A polyethylene pot having an area of 1/8850 are was charged with the alluvial clay loam of a rice field, and the soil was fertilized and plowed while adding an appropriate amount of water thereto. On the thus-prepared soil, the seeds of Panicum crusgalli were sown. The seeds were mixed well with the soil in the surface layer of 1 cm, and the water was maintained at a depth of 3.5 cm.

Thereafter, the pots were placed in a greenhouse, and when Echinochloa crus-galli reached the respectively predetermined leaf stages, granules which contained the respective compounds of the present invention as the active ingredient and which had been obtained in the same way as in Formulation Example 2 were dropped to the flooded surfaces. For comparison, granules which contained Comparative Compound A and Comparative Compound B, respectively, as the active ingredient, and which had been obtained in the same way as in Formulation Example 2 were dropped to the flooded surfaces. The doses of granules used were respectively so determined that the doses of active ingredients contained were 10 g, 5 g and 2.5 g, respectively per are.

On the 28th day after the herbicidal treatment, the herbicidal effect was observed, and the results are shown in Table 4.

The evaluation of the herbicidal effect was represented in accordance with the same criteria as in Experiment 1.

TABLE 4

| Compound No. | Dose of active ingredient g/a | Herbicidal effect on Echinochloa crus-galli by growing stages | | |
|---|---|---|---|---|
| | | 1–1.2th leaf stage | 1.5–2th leaf stage | 2–2.5th leaf stage |
| 1 | 10 | 5 | 5 | 5 |
| | 5 | 5 | 5 | 5 |
| | 2.5 | 5 | 5 | 5 |
| 3 | 10 | 5 | 5 | 5 |
| | 5 | 5 | 5 | 5 |
| | 2.5 | 5 | 5 | 5 |
| 4 | 10 | 5 | 5 | 5 |
| | 5 | 5 | 5 | 5 |
| | 2.5 | 5 | 5 | 5 |
| 7 | 10 | 5 | 5 | 5 |
| | 5 | 5 | 5 | 5 |
| | 2.5 | 5 | 5 | 5 |
| 10 | 10 | 5 | 5 | 5 |
| | 5 | 5 | 5 | 5 |
| | 2.5 | 5 | 5 | 5 |
| 13 | 10 | 5 | 5 | 5 |
| | 5 | 5 | 5 | 5 |
| | 2.5 | 5 | 5 | 4 |
| 14 | 10 | 5 | 5 | 5 |
| | 5 | 5 | 5 | 5 |
| | 2.5 | 5 | 5 | 5 |
| 15 | 10 | 5 | 5 | 5 |
| | 5 | 5 | 5 | 5 |
| | 2.5 | 5 | 5 | 4 |
| 16 | 10 | 5 | 5 | 5 |
| | 5 | 5 | 5 | 5 |
| | 2.5 | 5 | 5 | 5 |
| 17 | 10 | 5 | 5 | 5 |
| | 5 | 5 | 5 | 5 |
| | 2.5 | 5 | 5 | 4 |
| 19 | 10 | 5 | 5 | 5 |
| | 5 | 5 | 5 | 5 |
| | 2.5 | 5 | 5 | 4 |
| 20 | 10 | 5 | 5 | 5 |
| | 5 | 5 | 5 | 4 |
| | 2.5 | 5 | 3 | 3 |
| 21 | 10 | 5 | 5 | 5 |
| | 5 | 5 | 5 | 5 |
| | 2.5 | 5 | 5 | 5 |
| 29 | 10 | 5 | 5 | 5 |
| | 5 | 5 | 5 | 5 |
| | 2.5 | 5 | 5 | 4 |
| 30 | 10 | 5 | 5 | 5 |

TABLE 4-continued

| Compound No. | Dose of active ingredient g/a | Herbicidal effect on Echinochloa crus-galli by growing stages | | |
|---|---|---|---|---|
| | | 1–1.2th leaf stage | 1.5–2th leaf stage | 2–2.5th leaf stage |
| | 5 | 5 | 5 | 4 |
| | 2.5 | 5 | 3 | 2 |
| 31 | 10 | 5 | 5 | 5 |
| | 5 | 5 | 5 | 5 |
| | 2.5 | 5 | 5 | 5 |
| 36 | 10 | 5 | 5 | 4 |
| | 5 | 5 | 4 | 3 |
| | 2.5 | 4 | 4 | 2 |
| 37 | 10 | 5 | 5 | 5 |
| | 5 | 5 | 5 | 5 |
| | 2.5 | 5 | 5 | 5 |
| 44 | 10 | 5 | 5 | 5 |
| | 5 | 5 | 5 | 5 |
| | 2.5 | 5 | 5 | 4 |
| 47 | 10 | 5 | 5 | 5 |
| | 5 | 5 | 5 | 5 |
| | 2.5 | 5 | 5 | 5 |
| 48 | 10 | 5 | 5 | 5 |
| | 5 | 5 | 5 | 5 |
| | 2.5 | 5 | 5 | 5 |
| 49 | 10 | 5 | 5 | 5 |
| | 5 | 5 | 5 | 5 |
| | 2.5 | 5 | 5 | 5 |
| 51 | 10 | 5 | 5 | 5 |
| | 5 | 5 | 5 | 5 |
| | 2.5 | 5 | 5 | 5 |
| 53 | 10 | 5 | 5 | 5 |
| | 5 | 5 | 5 | 5 |
| | 2.5 | 5 | 5 | 5 |
| 55 | 10 | 5 | 5 | 5 |
| | 5 | 5 | 5 | 5 |
| | 2.5 | 5 | 5 | 5 |
| 56 | 10 | 5 | 5 | 5 |
| | 5 | 5 | 5 | 4 |
| | 2.5 | 5 | 4 | 2 |
| 58 | 10 | 5 | 5 | 5 |
| | 5 | 5 | 4 | 4 |
| | 2.5 | 5 | 3 | 2 |
| 59 | 10 | 5 | 5 | 5 |
| | 5 | 5 | 5 | 5 |
| | 2.5 | 5 | 5 | 5 |
| 61 | 10 | 5 | 5 | 5 |
| | 5 | 5 | 5 | 5 |
| | 2.5 | 5 | 5 | 5 |
| 62 | 10 | 5 | 5 | 5 |
| | 5 | 5 | 5 | 5 |
| | 2.5 | 5 | 5 | 5 |
| 64 | 10 | 5 | 5 | 5 |
| | 5 | 5 | 5 | 5 |
| | 2.5 | 5 | 5 | 5 |
| 65 | 10 | 5 | 5 | 5 |
| | 5 | 5 | 5 | 5 |
| | 2.5 | 5 | 4 | 4 |
| 71 | 10 | 5 | 5 | 5 |
| | 5 | 5 | 5 | 5 |
| | 2.5 | 5 | 5 | 4 |
| 72 | 10 | 5 | 5 | 5 |
| | 5 | 5 | 5 | 3 |
| | 2.5 | 5 | 4 | 2 |
| 75 | 10 | 5 | 5 | 5 |
| | 5 | 5 | 5 | 5 |
| | 2.5 | 5 | 5 | 5 |
| 76 | 10 | 5 | 5 | 4 |
| | 5 | 5 | 4 | 3 |
| | 2.5 | 4 | 4 | 2 |
| 79 | 10 | 5 | 5 | 5 |
| | 5 | 5 | 5 | 5 |
| | 2.5 | 5 | 4 | 4 |
| 81 | 10 | 5 | 5 | 5 |
| | 5 | 5 | 5 | 5 |
| | 2.5 | 5 | 5 | 5 |
| 82 | 10 | 5 | 5 | 5 |
| | 5 | 5 | 5 | 5 |
| | 2.5 | 5 | 5 | 5 |
| 83 | 10 | 5 | 5 | 5 |
| | 5 | 5 | 5 | 5 |
| | 2.5 | 5 | 5 | 5 |
| 85 | 10 | 5 | 5 | 5 |
| | 5 | 5 | 5 | 4 |
| | 2.5 | 5 | 4 | 3 |
| 88 | 10 | 5 | 5 | 5 |
| | 5 | 5 | 5 | 5 |
| | 2.5 | 5 | 5 | 4 |
| 89 | 10 | 5 | 5 | 5 |
| | 5 | 5 | 4 | 4 |
| | 2.5 | 5 | 4 | 2 |
| 91 | 10 | 5 | 5 | 5 |
| | 5 | 5 | 5 | 5 |
| | 2.5 | 5 | 5 | 5 |
| 94 | 10 | 5 | 5 | 5 |
| | 5 | 5 | 5 | 4 |
| | 2.5 | 5 | 4 | 4 |
| 95 | 10 | 5 | 5 | 5 |
| | 5 | 5 | 5 | 5 |
| | 2.5 | 5 | 5 | 5 |
| 98 | 10 | 5 | 5 | 5 |
| | 5 | 5 | 5 | 5 |
| | 2.5 | 5 | 5 | 4 |
| Comparative Compound A | 10 | 0 | 0 | 0 |
| | 5 | 0 | 0 | 0 |
| | 2.5 | 0 | 0 | 0 |
| Comparative Compound B | 10 | 5 | 3 | 0 |
| | 5 | 3 | 0 | 0 |
| | 2.5 | 0 | 0 | 0 |
| Untreated plot | — | 0 | 0 | 0 |

Experiment 3

Upland preemergence test

A plastic vat having an area of 1/2500 are was charged with the ash soil of a farmland, and the soil was fertilized. The seeds of crops soybean, cotton and wheat were sown and covered with a layer of the soil of 2 to 3 cm deep. The surface of the soil was uniformly covered with the soil which had been mixed with the seeds of weeds Echinochloa crus-galli, Digitaria adscendens, Alopecurus aequalis and Cyperus microiria. Wettable powders which contained the compounds shown in Table 5 as the active ingredient and which had been obtained in the same way as in Formulation Example 1 and wettable powders which contained Comparative Compound A and Comparative Compound B, respectively, as the active ingredient and which had been obtained in the same way as in Formulation Example 1 were diluted with water. These herbicides were uniformly sprayed by a small-sized power pressure atomizer onto the surfaces of the soil so that the doses of active ingredients contained were 20 g, 10 g and 5 g, respectively, per are.

On the 21th day after the herbicidal treatment, the herbicidal effect and the phytotoxicity to each crop were observed, and the results are shown in Table 4. The evaluation of the herbicidal effect and degree of damage were represented in accordance with the same criteria as in Experiment 1.

TABLE 5

| Compound No. | Dose of active ingredient g/a | Herbicidal effect | | | | Damage to crop | | |
|---|---|---|---|---|---|---|---|---|
| | | Echinochloa crus-galli | Digitaria adscendens | Alopecurus aequalis | Cyperus microiria | Soybean | Cotton | Wheat |
| 16 | 20 | 5 | 5 | 5 | 5 | 0 | 0 | 0 |
| | 10 | 4 | 5 | 4 | 5 | 0 | 0 | 0 |
| | 5 | 3 | 4 | 3 | 4 | 0 | 0 | 0 |
| 30 | 20 | 5 | 5 | 5 | 5 | 0 | 0 | 0 |
| | 10 | 4 | 5 | 4 | 4 | 0 | 0 | 0 |
| | 5 | 3 | 3 | 2 | 3 | 0 | 0 | 0 |
| 31 | 20 | 5 | 5 | 5 | 5 | 0 | 0 | 0 |
| | 10 | 4 | 5 | 4 | 5 | 0 | 0 | 0 |
| | 5 | 3 | 4 | 3 | 4 | 0 | 0 | 0 |
| 33 | 20 | 5 | 5 | 5 | 5 | 0 | 0 | 0 |
| | 10 | 4 | 5 | 4 | 5 | 0 | 0 | 0 |
| | 5 | 3 | 4 | 3 | 4 | 0 | 0 | 0 |
| 37 | 20 | 5 | 5 | 5 | 5 | 0 | 0 | 0 |
| | 10 | 4 | 5 | 4 | 5 | 0 | 0 | 0 |
| | 5 | 3 | 4 | 3 | 4 | 0 | 0 | 0 |
| 42 | 20 | 5 | 5 | 5 | 5 | 0 | 0 | 1 |
| | 10 | 4 | 5 | 4 | 5 | 0 | 0 | 0 |
| | 5 | 4 | 4 | 3 | 4 | 0 | 0 | 0 |
| 43 | 20 | 5 | 5 | 5 | 5 | 0 | 0 | 1 |
| | 10 | 4 | 5 | 4 | 4 | 0 | 0 | 0 |
| | 5 | 3 | 4 | 3 | 4 | 0 | 0 | 0 |
| 44 | 20 | 5 | 5 | 5 | 5 | 0 | 0 | 2 |
| | 10 | 5 | 5 | 4 | 5 | 0 | 0 | 0 |
| | 5 | 4 | 4 | 4 | 4 | 0 | 0 | 0 |
| 45 | 20 | 5 | 5 | 5 | 5 | 0 | 0 | 1 |
| | 10 | 5 | 5 | 5 | 5 | 0 | 0 | 0 |
| | 5 | 3 | 4 | 3 | 4 | 0 | 0 | 0 |
| 46 | 20 | 5 | 5 | 5 | 5 | 0 | 0 | 1 |
| | 10 | 4 | 5 | 4 | 4 | 0 | 0 | 0 |
| | 5 | 3 | 4 | 3 | 4 | 0 | 0 | 0 |
| 47 | 20 | 5 | 5 | 5 | 5 | 0 | 0 | 0 |
| | 10 | 4 | 5 | 4 | 4 | 0 | 0 | 0 |
| | 5 | 3 | 4 | 3 | 4 | 0 | 0 | 0 |
| 51 | 20 | 5 | 5 | 5 | 5 | 0 | 0 | 1 |
| | 10 | 5 | 5 | 5 | 5 | 0 | 0 | 0 |
| | 5 | 4 | 5 | 4 | 4 | 0 | 0 | 0 |
| 59 | 20 | 5 | 5 | 5 | 5 | 0 | 0 | 0 |
| | 10 | 4 | 5 | 4 | 5 | 0 | 0 | 0 |
| | 5 | 3 | 4 | 3 | 4 | 0 | 0 | 0 |
| 62 | 20 | 5 | 5 | 5 | 5 | 0 | 0 | 0 |
| | 10 | 4 | 5 | 4 | 4 | 0 | 0 | 0 |
| | 5 | 3 | 4 | 3 | 4 | 0 | 0 | 0 |
| 71 | 20 | 5 | 5 | 5 | 5 | 0 | 0 | 1 |
| | 10 | 4 | 5 | 4 | 5 | 0 | 0 | 0 |
| | 5 | 3 | 4 | 3 | 4 | 0 | 0 | 0 |
| 82 | 20 | 5 | 5 | 5 | 5 | 0 | 0 | 0 |
| | 10 | 5 | 5 | 4 | 5 | 0 | 0 | 0 |
| | 5 | 3 | 4 | 3 | 4 | 0 | 0 | 0 |
| 83 | 20 | 5 | 5 | 5 | 5 | 0 | 0 | 0 |
| | 10 | 4 | 5 | 5 | 4 | 0 | 0 | 0 |
| | 5 | 3 | 4 | 3 | 4 | 0 | 0 | 0 |
| 87 | 20 | 5 | 5 | 5 | 5 | 0 | 0 | 0 |
| | 10 | 4 | 5 | 4 | 5 | 0 | 0 | 0 |
| | 5 | 4 | 5 | 3 | 4 | 0 | 0 | 0 |
| 89 | 20 | 5 | 5 | 5 | 5 | 0 | 0 | 0 |
| | 10 | 3 | 5 | 3 | 4 | 0 | 0 | 0 |
| | 5 | 2 | 4 | 2 | 3 | 0 | 0 | 0 |
| 100 | 20 | 5 | 5 | 5 | 5 | 0 | 0 | 0 |
| | 10 | 4 | 5 | 4 | 5 | 0 | 0 | 0 |
| | 5 | 3 | 4 | 3 | 4 | 0 | 0 | 0 |
| Comparative Compound A | 20 | 0 | 0 | 0 | 1 | 0 | 0 | 0 |
| | 10 | 0 | 0 | 0 | 0 | 0 | 0 | 0 |
| | 5 | 0 | 0 | 0 | 0 | 0 | 0 | 0 |
| Comparative Compound B | 20 | 2 | 5 | 1 | 5 | 0 | 0 | 0 |
| | 10 | 0 | 3 | 0 | 4 | 0 | 0 | 0 |
| | 5 | 0 | 1 | 0 | 2 | 0 | 0 | 0 |
| Untreated plot | — | 0 | 0 | 0 | 0 | 0 | 0 | 0 |

Referential Example 1

Preparation of 3-[N-methyl-N-(p-toluenesulfonyl)amino]-2-(6-methylpyridin-2-yl)propene To a mixture of 1.48 g of N-methyl-p-toluenesulfonamide, 1.0 g of 2-chloro-6-(1-chloromethylvinyl)pyridine (Compound No. I - 3), 0.05 g of tetra-n-butylammonium bromide and 15 ml of toluene, 4.3 g of an aqueous solution of 40% sodium hydroxide was added, and the whole mixture was stirred at 80° C. for 3 hours. The reaction mixture was subsequently washed with water and brine and dried over anhydrous potassium carbonate. After the solvent was distilled off, the residue was purified by silica gel column chromatography (eluted with benzene - ethyl acetate 15:1) to obtain 1.5 g of Compound No. 216 in Table 6.

IR spectrum (neat) cm$^{-1}$: 1571, 1453, 1333, 1158, 1087.

'H-NMR spectrum (CCl$_4$-TMS)$^\delta$: 2.43 (3H, s), 2.50 (3H, s), 2.67 (3H, s), 4.13 (2H, s), 5.42 (1H, br, s), 6.07 (1H, br. s), 7.0 to 7.8 (7H, m).

Referential Example 2

Preparation of 2-(6-chloropyridin - 2-yl)-3-[N-methoxy-N-(p-toluenesulfonyl)amino]propene To a mixture of 1.80 g of N-methoxy-p-toluenesulfonamide, 1.85 g of 2-chloro-6-(l-chloromethylvinyl)-pyridine (Compound No. I-3), 0.06 g of tetra-n-butylammonium bromide and 18 ml of benzene, 4.4 g of an aqueous solution of 40% sodium hydroxide was added, and the whole mixture was stirred at 80° C. for 4 hours. The reaction mixture was subsequently washed with water and saturated saline solution and dried over anhydrous magnesium sulfate. After the solvent was distilled off, the residue was purified by silica gel column chromatography (eluted with benzene - ethyl acetate 20:1) to obtain 2.36 g of Compound No. 211 in Table 6.

IR spectrum (KBr) cm$^{-1}$: 1580, 1551, 1442, 1354, 1342 1159, 1130.

'H-NMR spectrum (CCl$_4$-TMS)$^\delta$: 2.50 (3H, s), 3.65 (3H, s), 3.87 (2H, s), 5.45 (1H, br. s), 6.42 (1H, d), 7.2 to 7.9 (7H, m).

Referential Example 3

Preparation of 2-(6-chloropyridin - 2-yl)-3-(N-methyl-N-ptolyloxysulfonylamino)propene 0.58 g of 50% sodium hydride dispersed in oil was washed with petroleum ether, and 10 ml of dry 1,2-dimethoxyethane was added thereto. A mixture of 2.01 g of p-tolyl N-methylsulfamate and 5 ml of dry 1,2-dimethoxyethane was then slowly added thereto under stirring at room temperature. The reaction mixture was ice cooled, and a mixture of 2.07 g of 2-chloro-6-(l-chloromethylvinyl)pyridine (Compound No. I-3) and 5 ml of dry 1,2-dimethoxyethane wad added dropwise thereto. After the mixture was stirred at room temperature for 2 hours, the solvent was distilled off. After saturated aqueous solution of ammonium chloride was added to the residue, the mixture was extracted with ethyl acetate. The organic layer was washed with water and was dried over anhydrous sodium sulfate. After the solvent was distilled off, the residue was purified by silica gel column chromatography (eluted with ethyl acetate - n-hexane 1:3) to obtain 2.17 g of Compound No. 210 in Table 6.

IR spectrum (neat) cm$^{-1}$: 1575, 1555, 1500, 1440, 1370, 1190, 1170, 1145, 860, 830, 795.

'H-NMR spectrum (CCl$_4$-TMS)$^\delta$: 2.37 (3H, s), 2.93 (3H, s), 4.35 (2H, obs. s), 5.60, 6.20 (1H, obs. s, each), 7.17 (4H, s), 7.20 (1H, dd), 7.48 to 7.72 (2H, m).

Referential Example 4

Preparation of N-methyl-N-[2-(6-methylsulfinylpyridin-2-yl)propen -3-yl]-5,6,7,8-tetrahydronaphthalene-2-sulfonamide 4.1 g of N-Bromosuccinimide was added under stirring to a mixture of 0.90 of N-methyl-N-[2-(6-methylthiopyridin-2-yl)-propen-3-yl]-5,6,7,8-tetrahydronaphthalene-2-sulfonamide obtained from N-methyl-(5,6,7,8-tetrahydronaphthalene)-2-sulfonamide and 2-(1-chloromethylvinyl)-6-methylthiopyridine (Compound No. I-11) in accordance with the procedure in Referential Example 2, 18 ml of tetrahydrofuran, 18 ml of dimethylsulfoxide and 9 ml of water. The whole mixture was stirred at room temperature for 8 hours. The reaction mixture was extracted with benzene after an aqueous solution of 10% sodium thiosulfate was added thereto. The extract was subsequently washed with water and brine and dried over anhydrous magnesium sulfate. After the solvent was distilled off, the residue was purified by silica gel column chromatography (eluted with benzene - ethyl acetate 3:1) to obtain 0.32 g of Compound No. 232 in Table 6.

IR spectrum (KBr) cm$^{-1}$: 1576, 1545, 1442, 1334, 1155, 1048.

'H-NMR spectrum (CDCl$_3$-TMS)$^\delta$: 1.7 to 2.0 (4H, m), 2.64 (3H, s), 2.90 (3H, s), 2.7 to 3.0 (4H, m), 3.96. (1H, d), 4.36 (1H, d), 5.57 (1H, br. s), 6.13 (1H, br. s), 7.2 to 8.1 (6H, m).

Referential Example 5

Preparation of 2-(6-chloropyridin - 2-yl)-3-[N-(4-methanesulfinyl-3-methylbenzenesulfonyl)-N-methylamino]propene 0.18 g of N-Bromosuccinimide was added to a mixture of 0.20 g of 2-(6-chloropyridin-2-yl)-3-[N-methyl-N-(3-methyl-4-methylthiobenzenesulfonyl)amino]propene obtained from N-methyl(3-methyl-4-methylthiobenzene)sulfonamide and 2-chloro-6(1-chloromethylvinyl)pyridine (Compound No. I-3) in accordance with the procedure in Referential Example 2 and 2 ml of methanol. The whole mixture was stirred at room temperature for 2 hours. The reaction mixture was extracted with chloroform after an aqueous solution of 10% sodium thiosulfate was added thereto. The extract was subsequently washed with water and brine and dried over anhydrous magnesium sulfate. After the solvent was distilled off, the residue was purified by silica gel column chromatography (eluted with chloroform - ethyl acetate 5:1) to obtain 0.10 g of Compound No. 225 in Table 6.

IR spectrum (neat) cm$^{-1}$: 1578, 1560, 1436, 1342, 1158, 1095, 1067, 1037.

'H-NMR spectrum (CDCl$_3$-TMS)$^\delta$: 2.45 (3H, s), 2.70 (3H, s), 2.73 (3H, s), 3.96 (1H, d), 4.18 (1H, d), 5.57 (1H, br. s), 6.13 (1H, br. s), 7.2 to 8.2 (6H, m).

Referential Example 6

Preparation of N-methyl-N-[2-(6-methylsulfonylpyridin-2-yl)propene-3-yl]-5,6,7,8-tetrahydronaphthalene-2-sulfonamide A mixture of 1.30 g of N-methyl-N-[2-(6-methylthiopyridin2-yl)propene-3-yl]-5,6,7,8-tetrahydronaphthalene-2-sulfonamide obtained from N-methyl-(5,6,7,8-tetrahydronaphthalene-2sulfonamide and 2-(1-chloromethylvinyl)-6-methylthiopyridine (Compound No. I-11) in accordance with the procedure in Referential Example 2, 0.23 g of sodium acetate trihydrate, 1.60 g of 40% peracetic acid and 13 ml of chloroform was stirred at room temperature for 2.5 hours. 13 ml of carbon tetrachloride was added to the reaction mixture, and the whole mixture was subsequently washed with water, an aqueous solution of 10% sodium bisulfite and brine in that order and dried over anhydrous magnesium sulfate. After the solvent was distilled off, the residue was crystallized and washed with a mixed solvent of ethyl acetate and n-hexane to obtain 1.30 g of Compound No. 233 in Table 6.

IR spectrum (KBr) cm$^{-1}$: 2932, 1585, 1452, 1325, 1155, 1120.

'H-NMR spectrum (CDCl$_3$-TMS)$^\delta$: 1.7 to 2.0 (4H, m), 2.63 (3H, s), 2.7 to 3.0 (4H, m), 3.29 (3H, s), 4.16 (2H, s), 5.60 (1H, br. s), 6.17 (1H, br. s), 7.2 to 8.1 (6H, m).

Examples of N-[2-(pyridyl)propen - 3-yl]-N-substituted sulfonamides synthesized from 1-(halogenomethyl)vinylpyridines according to the present invention in the same way as in Referential Examples 1 to 6 are shown in Table 6 together with Nos. of the Referential Examples adopted for preparation.

The structures of the compounds shown in Table 6 were confirmed by IR and 'H-NMR spectra.

4.07 (2H, br.s), 5.40, 6.16 (1H, br. s, each), 7.0 to 7.6 (6H, m).

What is claimed is:

1. A 1-(halogenomethyl)vinylpyridine represented by the following formula (V):

wherein u represents a halogen atom, and V represents a pyridyl group represented by the formula:

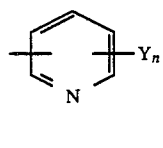

TABLE 6

| No. | X *2- | 3- | 4- | 5- | 6- | A | R | Bonding Position of Pyridyl group | Y | Melting point (°C.) or refractive index/°C. | Referential Example No. |
|---|---|---|---|---|---|---|---|---|---|---|---|
| 201 | H | H | H | H | H | CH=CH | CH$_3$ | 2- | 6-Cl | 114.5–116.5 | 1 |
| 202 | " | " | " | " | " | CH=CH | CH$_3$ | 2- | 6-CF$_3$ | 95–96 | 2 |
| 203 | " | " | " | " | " | NCH$_3$ | CH$_3$ | 2- | 6-Cl | 1.5816/25 | 3 |
| 204 | " | " | F | " | " | — | C$_2$H$_5$ | 2- | 6-Cl | 1.5698/25 | 1 |
| 205 | " | " | Cl | " | " | — | CH$_3$ | 2- | 6-Cl | 91–92 | 1 |
| 206 | " | " | CH$_3$ | " | " | — | CH$_3$ | 2- | H | 1.5757/25 | 1 |
| 207 | " | " | CH$_3$ | " | " | — | CH$_3$ | 2- | 4-Cl | 79–81 | 1 |
| 208 | " | " | CH$_3$ | " | " | — | CH$_3$ | 2- | 4-CH$_3$ | 82.5–84.5 | 1 |
| 209 | " | " | CH$_3$ | " | " | — | CH$_3$ | 2- | 6-Cl | 76–77 | 1 |
| 210 | " | " | CH$_3$ | " | " | O | CH$_3$ | 2- | 6-Cl | 1.5638/25 | 3 |
| 211 | " | " | CH$_3$ | " | " | — | OCH$_3$ | 2- | 6-Cl | 120.5–121 | 1 |
| 212 | " | " | CH$_3$ | " | " | — | CH$_2$CH=CH$_2$ | 2- | 6-Cl | 1.5761/25 | 2 |
| 213 | " | " | CH$_3$ | " | " | — | CH$_2$C≡CH | 2- | 6-Cl | 1.5749/25 | 2 |
| 214 | " | " | CH$_3$ | " | " | — | CH$_2$CF$_3$ | 2- | 6-Cl | 75–77 | 1 |
| 215 | " | " | CH$_3$ | " | " | — | CH$_3$ | 2- | 6-Br | 92–94 | 1 |
| 216 | " | " | CH$_3$ | " | " | — | CH$_3$ | 2- | 6-CH$_3$ | 77–79 | 1 |
| 217 | " | " | CH$_3$ | " | " | — | CH$_3$ | 2- | 6-OCH$_3$ | 81–82 | 2 |
| 218 | " | " | CH$_3$ | " | " | — | CH$_3$ | 4- | 2,6-Cl$_2$ | 126–127 | 2 |
| 219 | " | " | CH$_3$S | " | " | — | CH$_3$ | 2- | 6-Cl | 71–73 | 2 |
| 220 | " | CH$_3$ | Cl | " | " | — | CH$_3$ | 2- | 6-Cl | 79–80 | 1 |
| 221 | " | CH$_3$ | Cl | " | " | — | CH$_3$ | 2- | 6-CF$_3$ | 64–64.5 | 2 |
| 222 | " | CH$_3$ | Cl | " | " | — | CH$_3$ | 2- | 6-OCH$_3$ | 112–113 | 2 |
| 223 | " | CH$_3$ | Cl | " | " | — | CH$_3$ | 2- | 6-SCH$_3$ | 101–102 | 2 |
| 224 | " | CH$_3$ | Cl | " | " | — | CH$_3$ | 2- | 6-SO$_2$CH$_3$ | 110–113 | 6 |
| 225 | " | CH$_3$ | CH$_3$SO | " | " | — | CH$_3$ | 2- | 6-Cl | Amorphous solid | 5 |
| 226 | " | CH$_3$ | CH$_3$SO$_2$ | " | " | — | CH$_3$ | 3- | 5-Br | 127–128.5 | 1 |
| 227 | " | CH$_3$ | CH$_3$SO$_2$ | " | " | — | CH$_3$ | 4- | 2,6-Cl$_2$ | 143–144 | 2 |
| 228 | " | (CH$_2$)$_4$ | | " | " | — | CH$_3$ | 2- | 6-Cl | 94–94.5 | 1 |
| 229 | " | (CH$_2$)$_4$ | | " | " | — | CH$_3$ | 2- | 6-CF$_3$ | 90–90.5 | 2 |
| 230 | " | (CH$_2$)$_4$ | | " | " | — | CH$_3$ | 2- | 6-OCH$_3$ | 59.5–61 | 3 |
| 231 | " | (CH$_2$)$_4$ | | " | " | — | CH$_3$ | 2- | 6-SCH$_3$ | Amorphous solid | 2 |
| 232 | " | (CH$_2$)$_4$ | | " | " | — | CH$_3$ | 2- | 6-SOCH$_3$ | 152–154 | 4 |
| 233 | " | (CH$_2$)$_4$ | | " | " | — | CH$_3$ | 2- | 6-SO$_2$CH$_3$ | 155–160 | 6 |
| 234 | " | (CH$_2$)$_4$ | | " | " | — | CH$_3$ | 4- | 2,6-Cl$_2$ | 101–102 | 2 |

*2-, 3-, 4-, 5- and 6- represent the substitution position of X in a benzene ring The 'H-NMR spectra data on Compound No. 231 which was obtained in the form of amorphous solid is as follows:

No. 231 'H-NMR spectrum (CCl$_4$-TMS)$^\delta$: 1.7 to 2.0 (4H, m), 2.53 (3H, s), 2.60 (3H, s), 2.7 to 3.0 (4H, m), wherein Y represents a halogen atom, an alkyl group having 1 to 4 carbon atoms, a haloalkyl group having 1 to 2 carbon atoms, an alkoxy group having 1 to 4 carbon atoms, a haloalkoxy group having 1 to 2 carbon atoms or a group represented by S(O)$_q$T (wherein T represents an alkyl group having 1 to 4 carbon atoms and q is 0, 1 or 2), $Y_n$ may be the same or different from each other, and n represents 0, 1 or 2.

2. A compound according to claim 1, wherein V is a pyridyl group represented by the formula:

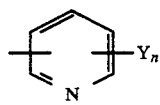

wherein Y represents a halogen atom, an alkyl group having 1 to 4 carbon atoms, a haloalkyl group having 1 to 2 carbon atoms, an alkoxy group having 1 to 4 carbon atoms or a group represented by S(O)qT (wherein T represents an alkyl group having 1 to 4 carbon atoms and q is 0), Yn may be the same or different from each other, and n represents 0, 1 or 2.

3. A compound according to claim 2, wherein V is a pyridyl group represented by the formula:

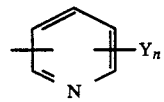

wherein Y represents a halogen atom, an alkyl group having 1 to 2 carbon atoms, a haloalkyl group having 1 to 2 carbon atoms, an alkoxy group having 1 to 2 carbon atoms or a group represented by S(O)qT (wherein T represents an alkyl group having 1 to 2 carbon atoms, and q is 0) Yn may be the same or different from each other, and n represents 0, 1 or 2.

4. A compound according to claim 1, wherein u is a chlorine atom, a bromine atom or an iodine atom, and V is a pyridyl group represented by the formula:

wherein Y represents a fluorine atom, a chlorine atom, a bromine atom, a methyl group, an ethyl group, a trifluoromethyl group, a chlorodifluoromethyl group, a dichlorofluoromethyl group, a trichloromethyl group, a methoxy group, an ethoxy group, a methylthio group or an ethylthio group, Yn may be the same or different from each other, and n represents 0, 1 or 2.

5. A compound according to claim 4, wherein u is a chlorine atom, a bromine atom or an iodine atom, and V is pyridyl group represented by the formula:

wherein Y represents a chlorine atom, a bromine atom, a methyl group, a trifluoromethyl group, a methoxy group or a methylthio group, Yn may be the same or different from each other, and n represents 0, 1 or 2.

* * * * *